(12) United States Patent
Khalef et al.

(10) Patent No.: US 9,244,029 B2
(45) Date of Patent: Jan. 26, 2016

(54) METHOD AND DEVICE FOR CONTROLLING CRYSTALLIZATION

(75) Inventors: Nawale Khalef, Meylan (FR); Aziz Bakri, Grenoble (FR)

(73) Assignee: UNIVERSITE JOSEPH FOURIER, Grenoble (FR)

( * ) Notice: Subject to any disclaimer, the term of this patent is extended or adjusted under 35 U.S.C. 154(b) by 1201 days.

(21) Appl. No.: 13/133,793

(22) PCT Filed: Dec. 10, 2009

(86) PCT No.: PCT/FR2009/052476
§ 371 (c)(1),
(2), (4) Date: Oct. 31, 2011

(87) PCT Pub. No.: WO2010/067028
PCT Pub. Date: Jun. 17, 2010

(65) Prior Publication Data
US 2012/0178923 A1    Jul. 12, 2012

(30) Foreign Application Priority Data
Dec. 10, 2008 (FR) ...................... 08 06918

(51) Int. Cl.
*C30B 29/54* (2006.01)
*G01N 25/14* (2006.01)
*B01D 9/00* (2006.01)

(52) U.S. Cl.
CPC ................ *G01N 25/147* (2013.01); *B01D 9/00* (2013.01)

(58) Field of Classification Search
USPC .................................. 117/4, 5, 7, 8, 932, 933
See application file for complete search history.

(56) References Cited

U.S. PATENT DOCUMENTS 5,360,478 A * 11/1994 Krukonis et al. ............... 117/68
2004/0166164 A1 * 8/2004 Savoir et al. .................. 424/489

OTHER PUBLICATIONS

Ahmed et al: "The use of isothermal microcalorimetry in the study of small degrees of amorphous content of a hydrophobic powder", International Journal of Pharmaceutics, Jan. 1, 1996, pp. 195-201, vol. 130, No. 2, XP000607240.

Angberg M et al: "Evaluation of heat-conduction microcalorimetry in pharmaceutical stability studies. V. A new approach for continuous measurements in abundant water vapour", International Journal of Pharmaceutics, vol. 81, No. 2-3, Mar. 31, 1992, pp. 153-167, XP025554446.

(Continued)

*Primary Examiner* — Robert M Kunemund
(74) *Attorney, Agent, or Firm* — Young & Thompson

(57) ABSTRACT

The use of a vapor source (10) in an isothermal system (8) to control the crystallization or recrystallization of a sample of solid material (9) which is initially at least partially amorphous and/or at least partially crystalline and contained within the system (8), the vapor source (10) including at least one solvent for crystallizing the solid material, the vapor diffusion (14) of which leads to the crystallization or recrystallization of the sample (9), the vapor source (10) being such that the quantities of heat exchanged within the system during the crystallization or recrystallization of the sample (9) other than the heat of crystallization or recrystallization of the sample are less than approximately 10%, particularly 5%, and advantageously 1% of the heat of crystallization or recrystallization of the sample. The vapor source (10) is preferably a pure solvent or a solvent mixture in which no solute is dissolved.

50 Claims, 16 Drawing Sheets

(56) References Cited

OTHER PUBLICATIONS

Shah et al: "Analytical techniques for quantification of amorphous/crystalline phases in pharmaceutical solids", Journal of Pharmaceutical Sciences, vol. 95, No. 8, Aug. 2006, pp. 1641-1665, XP002539677.

Khalef et al: "Etude comparative de cristallisation par calorimetrie isotherme en systeme ouvert et en systeme ferme et determination de faibles taux d'amorphe", Recents Progres en Genie des Procedes, No. 97, May 22, 2008, pp. 249-256, XP002548079.

International Search Report, dated Apr. 27, 2010, in PCT/FR2009/052476.

PCT/ISA/237—Written Opinion of the International Searching Authority, dated Apr. 27, 2010.

* cited by examiner

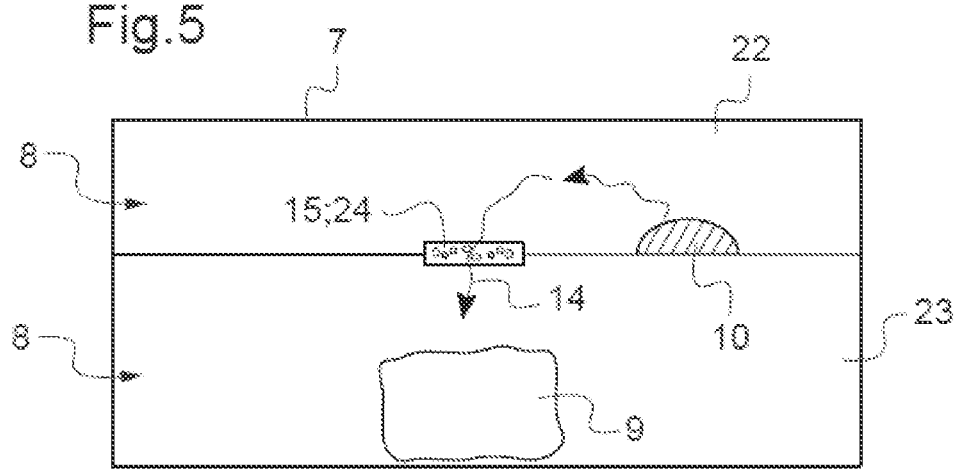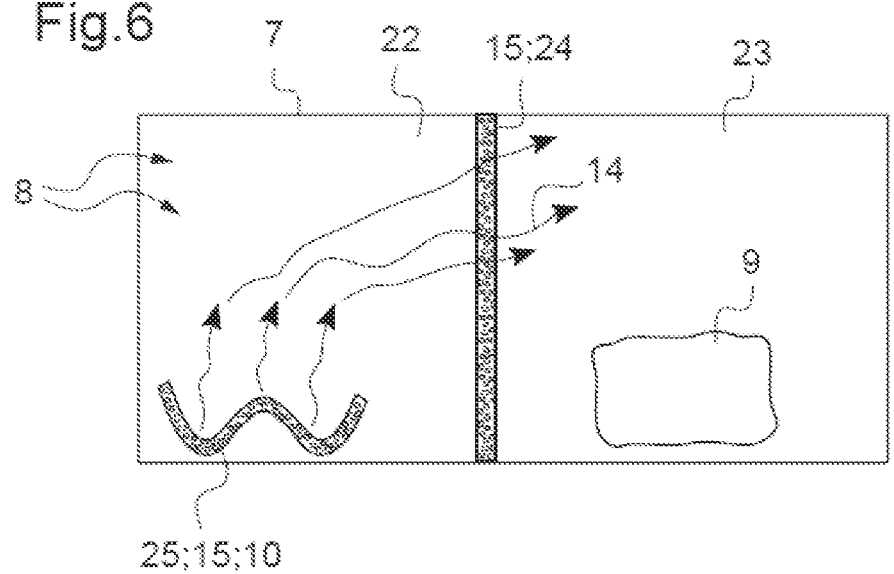

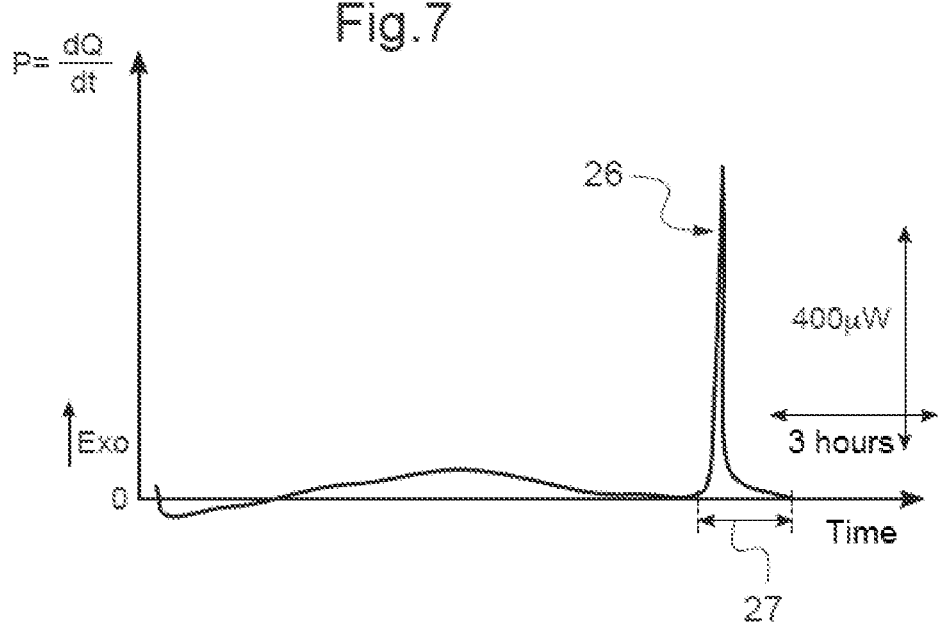
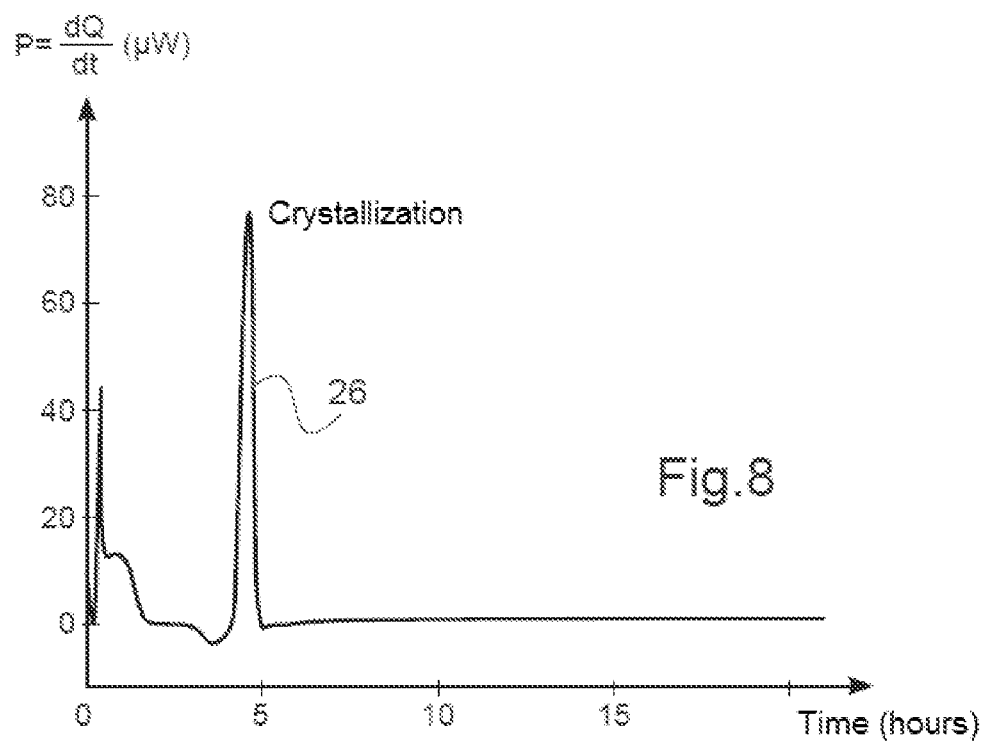

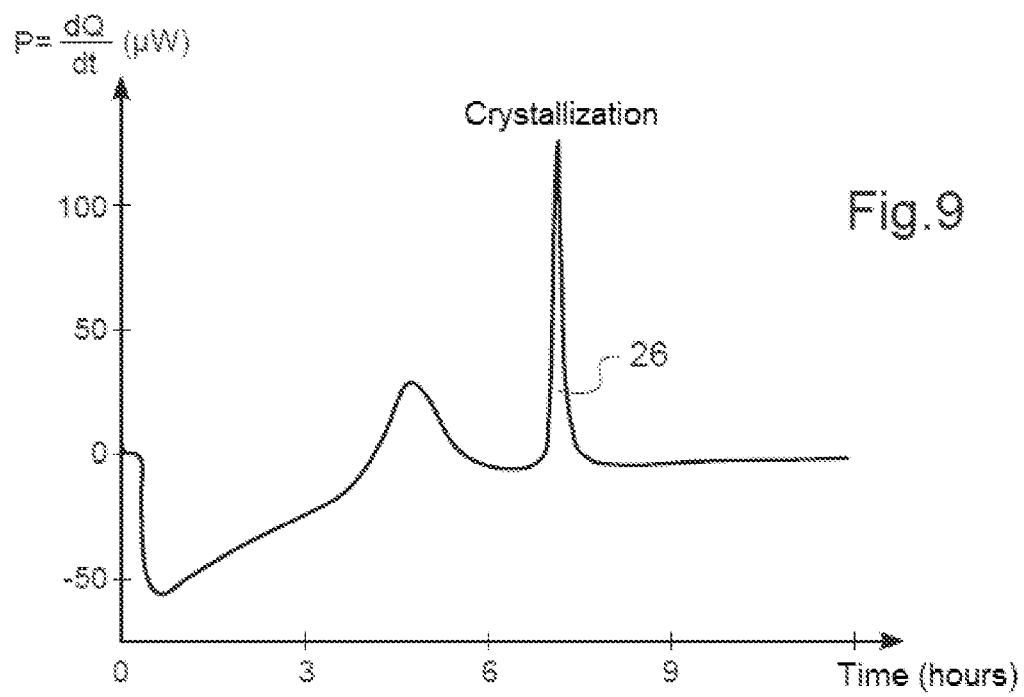
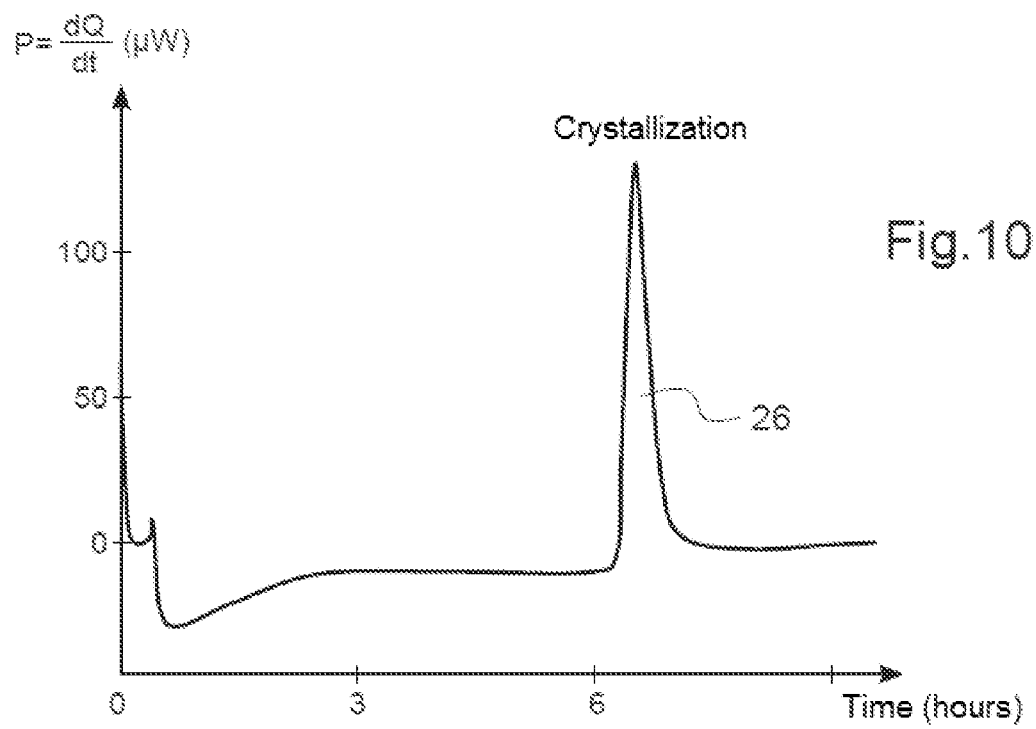

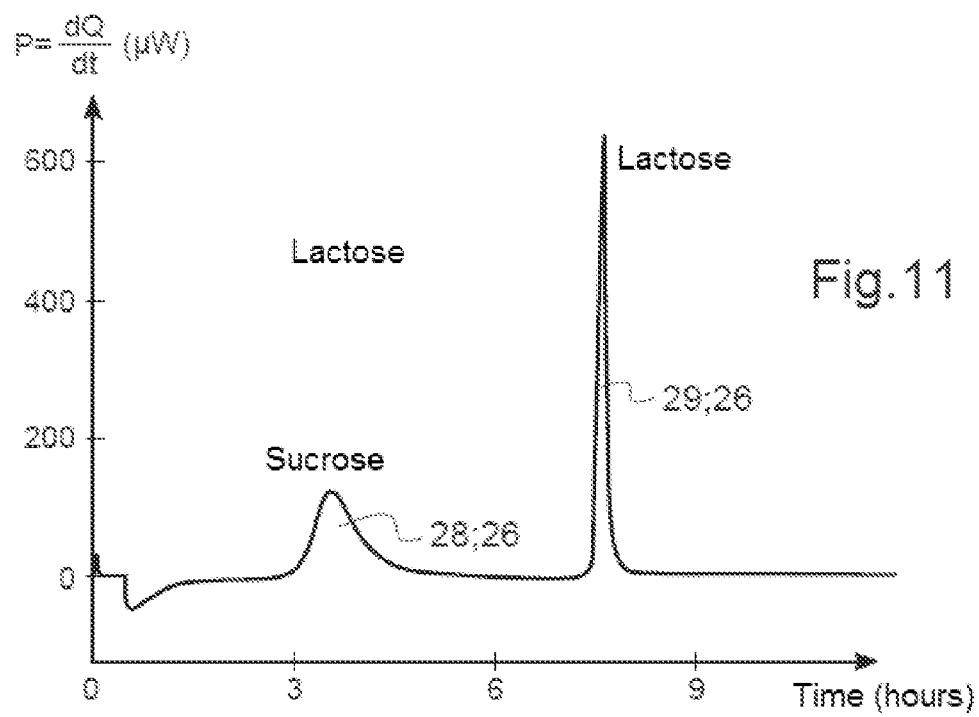
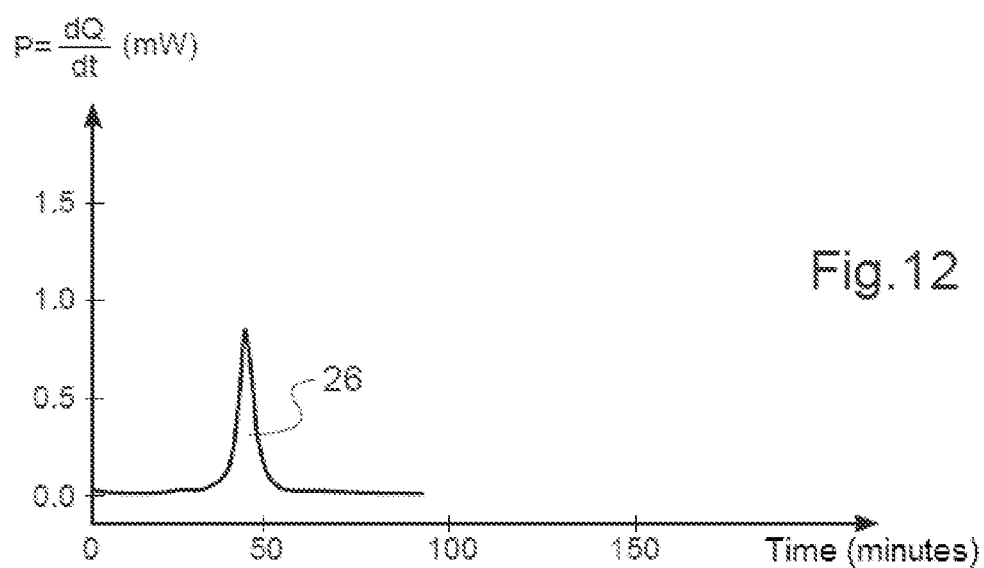

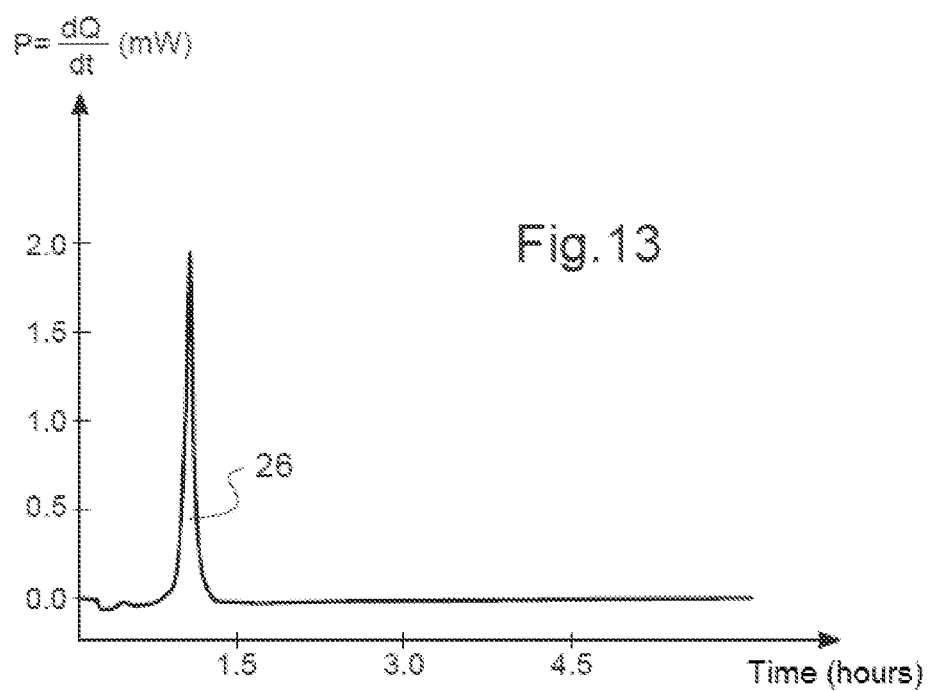
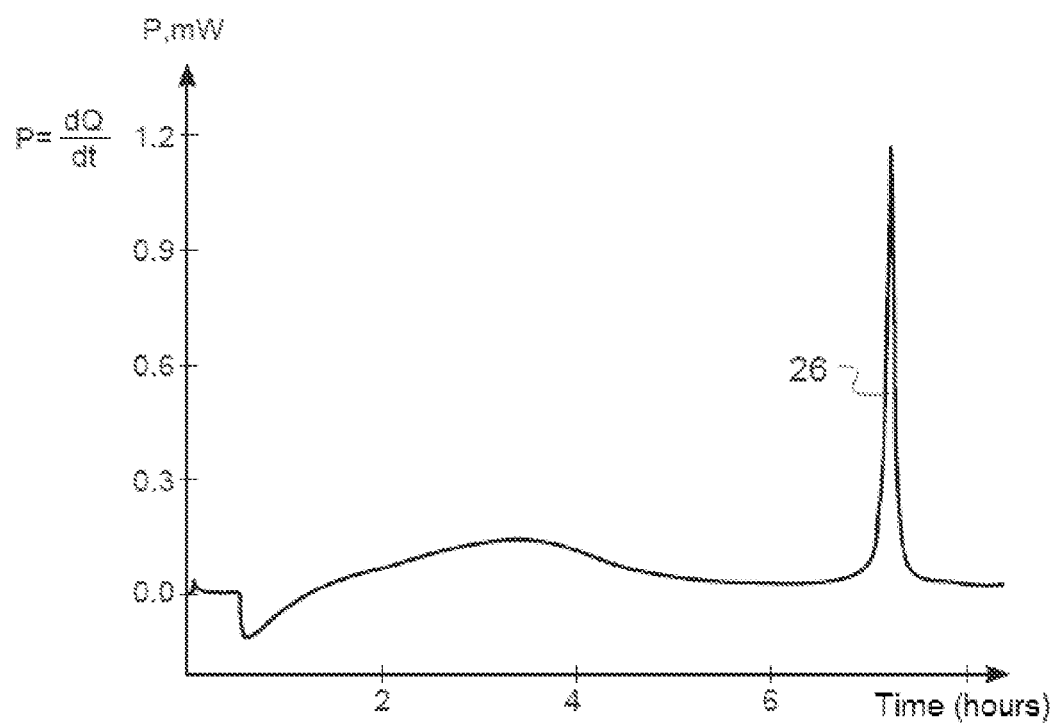

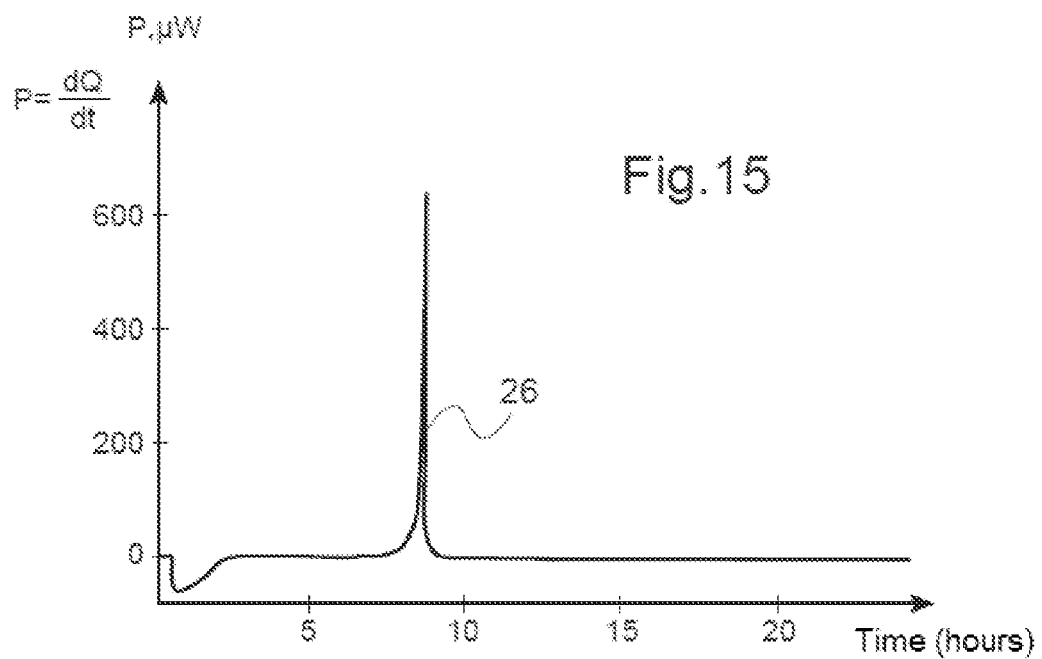
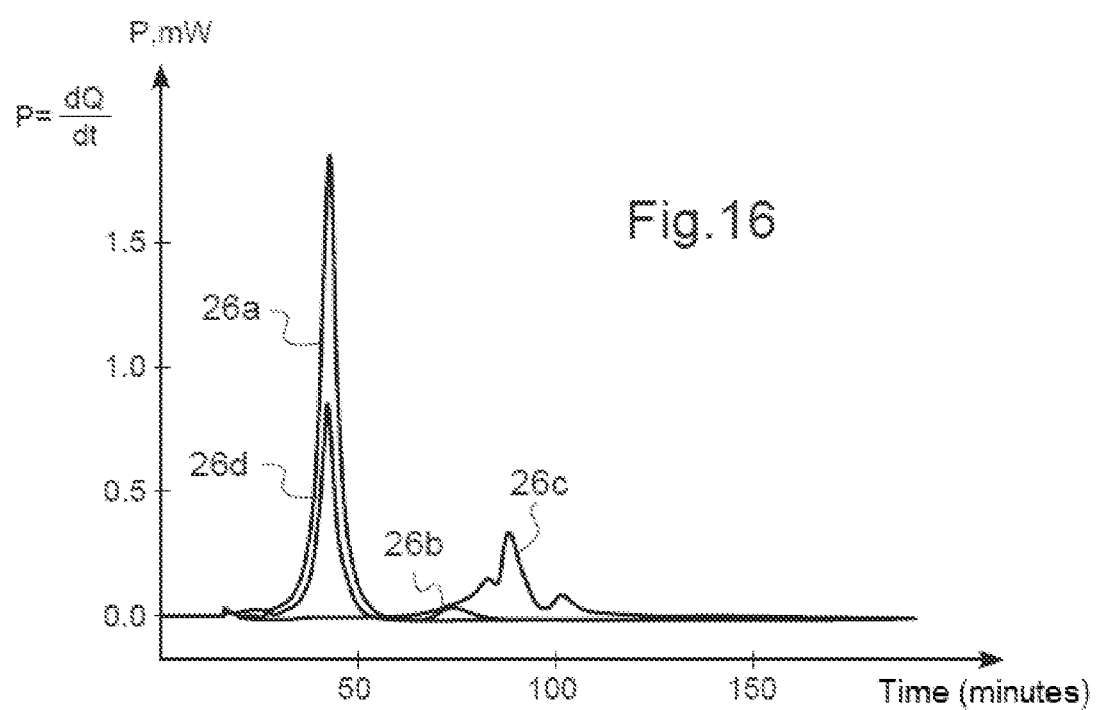

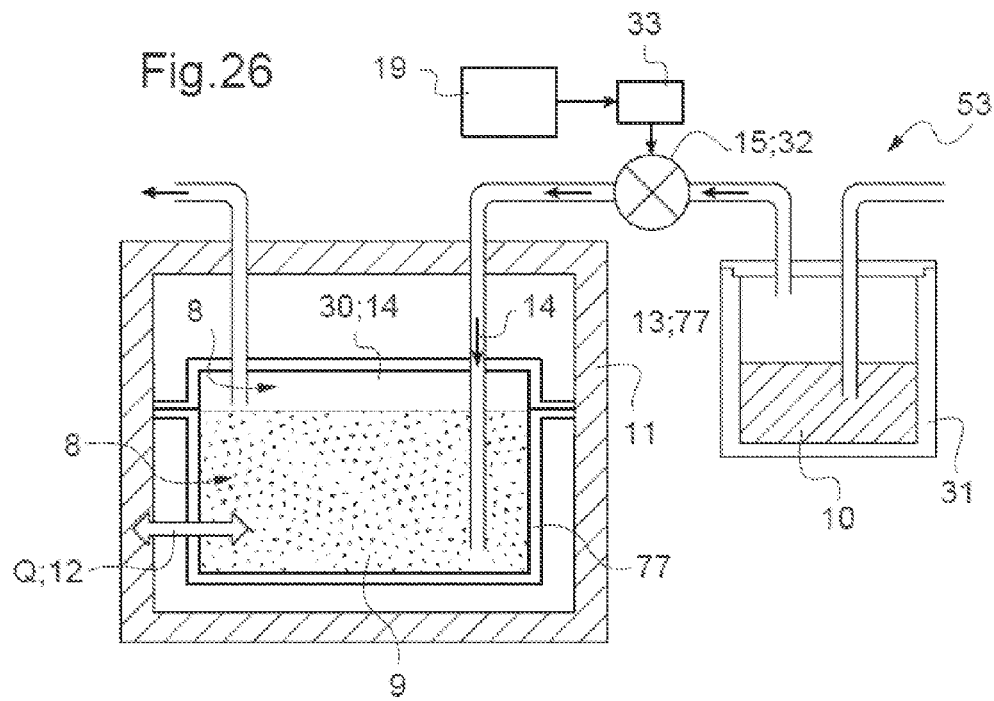
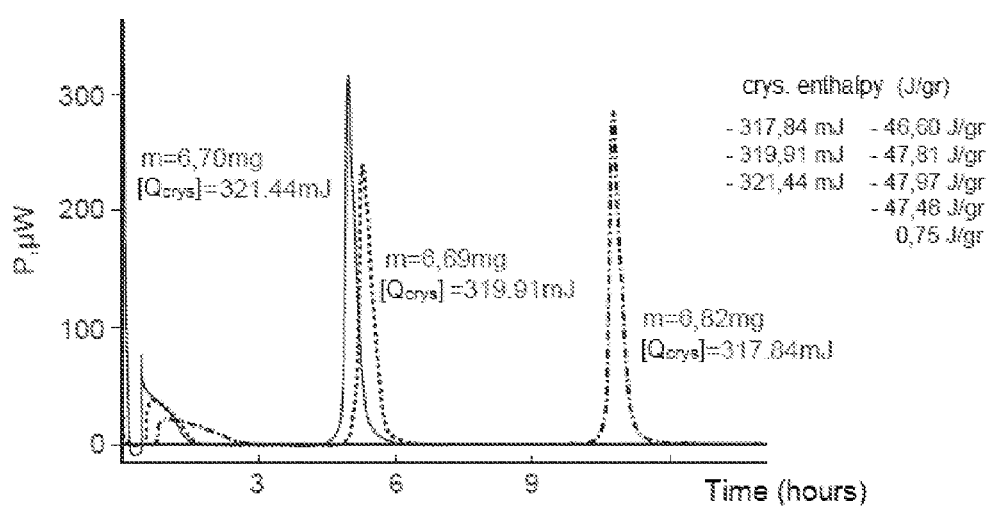

METHOD AND DEVICE FOR CONTROLLING CRYSTALLIZATION

TECHNICAL FIELD

The present invention relates to a method for controlling crystallization or recrystallization of a solid material. It also relates to a device implementing this method.

The technical field of the invention is more particularly but not limitatively the study, within a calorimeter, of the crystallization or recrystallization of a sample of solid material, in particular for determining an amorphous content of this sample, or for determining a crystalline phase content which recrystallizes, or also for optimizing the experimental crystallization conditions of this sample. The technical field can also extend to any system where controlling the rate (and/or of its variation) of introduction of molecules into the vapour state induces a physical or chemical or biological reaction in the sample, which can be measured by monitoring the heat flow that it generates.

PRIOR ART

During the last few years the pharmaceutical and agri-food industries have shown a particular interest in amorphous bodies. By amorphous body is meant a preferably solid amorphous body which is not crystallized. Amorphous materials are sought for their useful physico-chemical and mechanical properties, such as:

their solubility, as they exhibit better solubility than their crystalline homologues, or their viscoelastic property, used in particular in compression processes, or Often, their presence is undesirable due to their high molecular mobility, which gives them a greater physical and chemical instability than their crystalline homologue. This can have drastic consequences for the quality of the finished product, in particular if this product is in powder form. The amorphous material can be generated during individual operations such as grinding, lyophilization or nebulization. The amorphous material thus generated can undergo crystallization under the effect of moisture or temperature and cause agglomeration during the manufacture or storage of the product. For example, in the case of products intended for the pulmonary route, the presence of small quantities of amorphous material can cause the agglomeration of the particles with each other during inhalation, which prevents the active ingredient (AI) from reaching the pulmonary alveoli and thus reduces its therapeutic effect.

Research into and development of reliable methods for determining the amorphous content of raw materials or finished products have always been a constant concern of manufacturers in this field. Advantage is taken of the amorphous material's propensity to crystallize under the effect of temperature or pressure in order to measure the amorphous content of a product. Thermal analysis is one of the preferred methods for measuring the amorphous content.

A method is known for crystallizing a dry amorphous material at a constant temperature in a closed ampoule under relative humidity (RH) controlled by a saturator containing a saturated saline solution. The thermal activity traces (TT) of the phenomenon are monitored in an isothermal microcalorimeter (ITC). This method is widely adopted by manufacturers and particularly in the pharmaceutical sector, for determining low amorphous contents present in the raw materials or in a finished product. In such a method, a partially amorphous sample is placed in a closed calorimetric ampoule, to which an open saturator is added, which controls the desired humidity within the measuring ampoule. The assembly is introduced into a microcalorimeter, the ampoule remains in an equilibrium position for approximately 30 minutes, then it is lowered into a measuring position. The saturator contains a saturated salt water solution with a specific and constant water activity, thus imposing a fixed Relative Humidity (RH) in the vapour phase in the ampoule, above the sample. With reference to FIG. 1, as from the introduction of the saturator into the measuring ampoule, the dry and partially amorphous sample undergoes the following transformations:

reference phase 1: Hydration by the vapour phase: the dry sample adsorbs the humidity from the vapour phase in the ampoule. This phenomenon is exothermic. The water molecules evaporate from the saturator in order to keep the vapour pressure constant, and this phenomenon is endothermic. The thermal activity of the phenomenon during this water sorption phase on the amorphous material and evaporation of the saturator tends towards zero, as equilibrium becomes established.

reference phase 2: when the amorphous sample reaches its Critical Relative Humidity, it dissolves: this phenomenon is endothermic but is accompanied by hydration of the dissolved molecules (exothermic phenomenon). The overall heat can equally well appear endothermic or exothermic, depending on the properties of the sample analyzed.

reference phase 3: after dissolving, the sample recrystallizes and expels the absorbed water until it reaches its Critical Relative Humidity. The water expelled during the crystallization of the amorphous material evaporates, causing an increase in the Relative Humidity of the vapour phase in the ampoule beyond the value fixed by the saturator. This is followed by condensation of the water from the vapour phase in the saturator until equilibrium is reached. At equilibrium, the Relative Humidity in the ampoule is fixed by the saturator. The mass of water expelled and condensed in the saturator therefore corresponds to the difference between the water content of the amorphous material and that of the crystalline material at crystallization humidity. It is variable from one measurement to the other as it depends on the mass of the amorphous material in the sample.

This method according to the state of the art comprises:

a measurement of the thermal activity dQ/dt in the ampoule within the microcalorimeter, said measurement producing a curve such as that shown in FIG. 1, and deduction of the quantity of heat $Q_{tot}$ received or given up by the system comprised in the ampoule during phase 3, by integration of the thermal activity over the time interval 4 corresponding to the thermal activity peak of phase 3, determination of the mass m of amorphous material in the sample.

The heat of evaporation and condensation of the expelled water being equal in absolute value, the heat $Q_{tot}$ measured during this phase 3 is assigned by the state of the art to the heat of crystallization of the amorphous material $Q_{crys}$ and therefore considered proportional to the mass of crystallized amorphous material according to the equation:

$$Q_{tot} = Q_{crys} = \Delta H_{crys} * m$$

Where $\Delta H_{crys}$ is the enthalpy of crystallization of the amorphous material. The mass m is therefore determined according to the equation:

$$m = Q_{crys}/\Delta H_{crys} = Q_{tot}/\Delta H_{crys}$$

The inventors have demonstrated that such a method for determining the mass m lacks accuracy, and propose a novel method and device making it possible to solve this problem of accuracy in determining the mass m of amorphous material in the sample.

DISCLOSURE OF THE INVENTION

This objective is achieved with the use of a vapour source in an isothermal system to control the crystallization or recrystallization of a sample of solid material that is initially at least partially amorphous and/or at least partially crystalline, contained in the vapour pressure system controlled by the vapour source, said vapour source comprising at least one solvent for crystallizing said solid material, the vapour diffusion of which leads to the crystallization or recrystallization of the sample, said vapour source being such that the quantities of heat exchanged within the system during the crystallization or recrystallization of the sample other than the heat of crystallization or recrystallization of the sample are less than approximately 10%, in particular 5%, advantageously 1% of the heat of crystallization or recrystallization of the sample.

The sample is preferably comprised in a cell such as for example an isothermal microcalorimetric ampoule or a DSC cup, and the internal volume of which is adjusted to the volume of the sample such that the dead volume of the cell is less than 5% of the volume of the sample.

According to the invention, the vapour can advantageously be injected directly inside the sample which is then preferably in powder form.

According to an advantageous embodiment, the isothermal system is closed. By closed system, is meant for example any hermetically sealed enclosure or sets of enclosures allowing an exchange of heat: calorimetric cell, DSC measurement cup etc.

By vapour pressure controlled by the vapour source is meant the fact of imposing or reaching the critical vapour pressure for the crystallization of the amorphous material by the appropriate vapour source, as defined hereafter.

The vapour source can comprise a solute dissolved in at least one crystallization solvent:
  said solute being in a quantity less than the quantity necessary for the saturation of the solute in said solvent, or
  said solute being at saturation in said solvent, the solute dissolved in said solvent having a crystallization latency time greater than a crystallization or recrystallization latency time of the sample such that the solute crystallizes only after the end of the crystallization or recrystallization of the sample.

According to an embodiment, said solute exhibits no heat of solvation in said solvent.

According to another embodiment, said solute is in a quantity less than the quantity necessary for the saturation of the solute in said solvent and said solute exhibits no heat of solvation in said solvent.

According to another embodiment, said solute being at saturation in said solvent, the solute dissolved in said solvent having a crystallization latency time greater than a crystallization or recrystallization latency time of the sample such that the solute crystallizes only after the end of the crystallization or recrystallization of the sample and said solute exhibits no heat of solvation in said solvent.

According to another embodiment of the invention, said solvent in the vapour source comprises no dissolved solute, and in particular the vapour source comprises no dissolved solute.

According to another embodiment of the invention, said solvent in the vapour source preferably comprises no dissolved salt, and in particular the vapour source comprises no dissolved salt.

In a variant, the vapour source can be a single pure solvent, preferably selected from pure water or an organic solvent such as methanol or ethanol.

By pure solvent is meant any aqueous or organic solvent allowing the crystallization of the amorphous material, such as methanol, ethanol, acetone, acetonitrile, n-propanol, n-butyl alcohol, THF, chloroform, toluene etc. This list is not exhaustive.

In another variant, the vapour source can comprise a mixture of solvents preferably selected from water or an organic solvent such as methanol, ethanol, acetone, acetonitrile, n-propanol, n-butyl alcohol, THF, chloroform, toluene etc. This list is not exhaustive.

In particular the mixture may be "methanol-ethanol" or "water-ethanol" or also "water-methanol" or "glycerol-methanol>>.

Generally the percentage of the advantageous mixture depends on the nature of the amorphous material to be crystallized and on the solvents used. In the case of "methanol-ethanol" or "water-ethanol" or also "water-methanol" mixtures, the crystallization of the lactose can take place in any proportions of the mixture. In the case of the "glycerol-methanol" mixture, sucrose crystallization has been observed only in the case of mixtures in which the percentage of methanol is greater than 65% by weight.

The sample of material can initially (i.e. before the crystallization or recrystallization of the sample) comprise:
  a purely amorphous sample,
  an initially polymorphic or pseudo-polymorphic crystal, recrystallization comprising passage of part or all of the sample from one crystalline phase to another crystalline phase, or
  an amorphous and crystalline mixture.

According to an embodiment of the invention, use preferably also comprises determination of the amorphous content of the sample.

The system (preferably closed) can comprise means of limiting and/or of controlling and/or of managing the diffusion of vapour, i.e. the vapour diffusion rate. By managing the diffusion rate of the vapour pressure from the vapour source, numerous disadvantages of the prior art are avoided. The limitation of the vapour diffusion is obtained by any physicochemical (e.g. diffusion through a membrane) or mechanical means (diameter, length of the diffusion capillary) utilized, in order to limit the sorption rate of said vapour on the sample. The means of limitation are preferably arranged so that the vapour diffusion rate is less than 100 nano moles per second.

The limitation of the diffusion rate can be arranged so that the crystallization or recrystallization commences only when the system has reached an equilibrium temperature and measurement of the heat of crystallization is not disturbed.

The vapour source can be contained in a capillary, and/or
The vapour source can be absorbed in a non-soluble support in said crystallization solvent, and/or
The vapour source can be contained in a reservoir separated from the sample by a porous wall limiting the vapour diffusion from the reservoir towards the sample of material.

According to yet another aspect of the invention, a method is proposed for controlling crystallization or recrystallization comprising:
  vapour diffusion of at least one crystallization solvent in an isothermal system, said system comprising a sample of solid material and a vapour source diffusing the vapour, the solid material being initially at least partially amorphous and/or at least partially crystalline,
crystallization or recrystallization of the sample under the effect of the diffused vapour,
at least during the crystallization or recrystallization, measurement of the heat received or given up by the system, the vapour source comprising said solvent for crystallizing said solid material, a method according to the invention in which during the crystallization or recrystallization the quantities of heat exchanged within the system other than the heat of crystallization or recrystallization of the sample are less than approximately 10%, in particular 5%, advantageously 1% of the heat of crystallization or recrystallization of the sample.

The sample is preferably comprised in a cell such as for example a microcalorimetric ampoule or a DSC cup, the internal volume of which is adjusted to the volume of the sample so that the dead volume of the cell is less than 5% of the volume of the sample.

Vapour can advantageously be injected directly inside the sample which is in powder form.

The vapour source can comprise a solute dissolved in said crystallization solvent:
said solute being in a quantity less than the quantity necessary for the saturation of the solute in said solvent, or
said solute being at saturation in said solvent, the solute dissolved in said solvent having a crystallization latency time greater than a crystallization or recrystallization latency time of the sample such that the solute crystallizes only after the end of crystallization or recrystallization of the sample, or
the vapour source comprising a solute dissolved in said crystallization solvent, said solute exhibiting no heat of solvation in said solvent.

The solute has the role of lowering the vapour pressure and being close to the critical pressure of crystallization of the amorphous material, whereas the limitation of the diffusion rate of the vapour makes it possible to prevent the sorption from taking place too rapidly and the sorption and crystallization phases from being merged, which prevents good integration. The limitation of the diffusion is essential whether a pure solvent or a solution with a solute is used.

The solute can be a solid which is soluble in the solvent or a liquid which is miscible in the solvent.

The solute can be of a kind identical to that of the sample of solid material to be crystallized or recrystallized as shown in FIG. 13 where a sample of sucrose is crystallized with a methanol solution saturated with sucrose, or also, a sample of lactose, crystallized with a methanol solution saturated with lactose shown in FIG. 14. The use of a solution saturated with solute of a kind identical to that of the sample has the advantage of maintaining the crystal formed under a vapour pressure which is sufficiently great to crystallize the amorphous material (the critical dissolution/crystallization vapour pressure of the amorphous material being less than the part of the sample already crystallized) and not to risk exposing the crystal formed to a vapour pressure greater than its critical dissolution pressure and therefore to risk dissolving the crystal during the crystallization phase.

If the critical dissolution vapour pressure "of the crystal formed" (the crystalline form of the sample to be crystallized) is known, any other solute can also be used at a concentration such that the vapour pressure imposed by the solution of said solute in the saturator does not exceed the critical dissolution vapour pressure of the part of the sample already crystallized as shown in FIG. 15, where a sample of sucrose is crystallized with a methanol solution saturated with lactose, the lactose being a solute of a different kind from the sample to be crystallized.

According to an embodiment of the method of the invention, said solvent in the vapour source comprises no dissolved solute.

According to another embodiment of the method of the invention, said solvent in the vapour source preferably comprises no dissolved salt.

In a variant, the vapour source can be a single pure solvent, preferably selected from pure water or an organic solvent such as methanol or ethanol.

In another variant, the vapour source is a mixture of solvents preferably selected from pure water or an organic solvent such as methanol or ethanol, in particular a "methanol-ethanol" or "water-ethanol" or also "water-methanol" mixture.

The sample of material can initially (i.e. before the crystallization or recrystallization of the sample) comprise:
a purely amorphous sample.
an initially polymorphic or pseudo-polymorphic crystal, the recrystallization comprising passage of part or all of the sample from one crystalline phase to another crystalline phase, or
an amorphous and crystalline mixture, The method according to the invention preferably also comprising determination of the amorphous content of the sample.

The heat measurement can comprise a measurement of the heat flow exchanged with the system or a measurement of the thermal activity of the system.

The method according to the invention can also comprise a limitation of the vapour diffusion rate in the system:
the vapour diffusion rate can be limited such that the vapour diffusion rate is less than 100 nano moles per second, and/or
the vapour diffusion can comprise a vapour diffusion of said at least one crystallization solvent contained in a capillary, and/or
the vapour diffusion can comprise a vapour diffusion of said crystallization solvent absorbed in a non-soluble support in this at least one solvent, and/or
the vapour diffusion can comprise a vapour diffusion of said crystallization solvent contained in a reservoir separated from the sample by a porous wall limiting the vapour diffusion from the reservoir towards the sample of material.

The method according to the invention can comprise, before the measurement, a stabilization of the temperature of the system until the system reaches an equilibrium temperature, the system remaining at this equilibrium temperature during the measurement, the limitation of the diffusion rate preferably being arranged so that the crystallization or recrystallization commences only when the system has reached the equilibrium temperature.

According to yet another aspect of the invention, a device for controlling crystallization or recrystallization is proposed, comprising:
means for receiving a sample of solid material initially at least partially amorphous and/or at least partially crystalline and for receiving a vapour source comprising at least one solvent for crystallizing said solid material, the reception means being arranged so that the sample of material and the vapour source form an isothermal system, the reception means being moreover arranged so that vapour diffused by the source initiates crystallization or recrystallization of the sample, and means for measuring heat received or given up by the system, the device according to the invention also comprising means for limiting the vapour diffusion rate in the system.

The means of limitation can be arranged so that the vapour diffusion rate is less than 100 nano moles per second.

The device according to the invention, and more particularly the reception means, can comprise a cell such as for example a microcalorimetric ampoule or a DSC pan, this cell being arranged for receiving the sample and so that its internal volume can be adjusted to the volume of the sample so that the dead volume of the cell is less than 5% of the volume of the sample.

The device according to the invention can also comprise means for injecting the vapour directly inside the sample which is in powder form.

The means of limitation of the diffusion rate can comprise:
- a capillary provided for containing the vapour source, and/or
- a non-soluble support in said solvent, provided for absorbing the vapour source, and/or
- a porous wall separating the sample and a reservoir provided for containing the vapour source, said wall being arranged to limit the vapour diffusion from the reservoir towards the sample of material.

The reception means can comprise means for stabilizing the temperature of the system until the system reaches an equilibrium temperature, the means of limitation of the diffusion rate preferably being arranged so that the crystallization or recrystallization of the sample commences only when the system has reached the equilibrium temperature.

The device according to the invention can also comprise means for determining an amorphous content of the sample, from a measurement carried out by the measurement means.

DESCRIPTION OF FIGURES AND EMBODIMENTS

Other advantages and features of the invention will become apparent on reading the detailed description of implementations and embodiments which are in no way limitative, and from the following attached drawings.

Figure 2A:
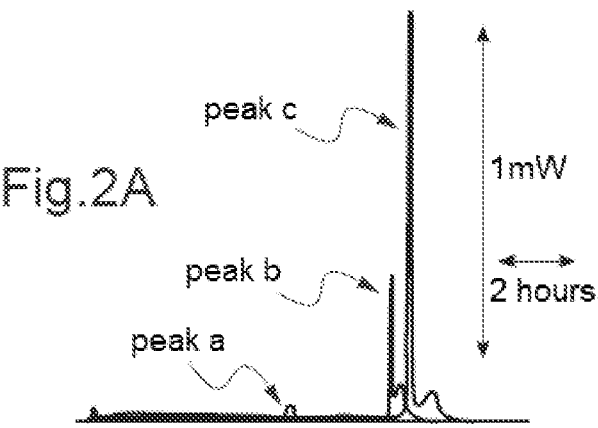
FIGS. 2A and 2B are obtained for different masses of amorphous material.
Figure 2B:
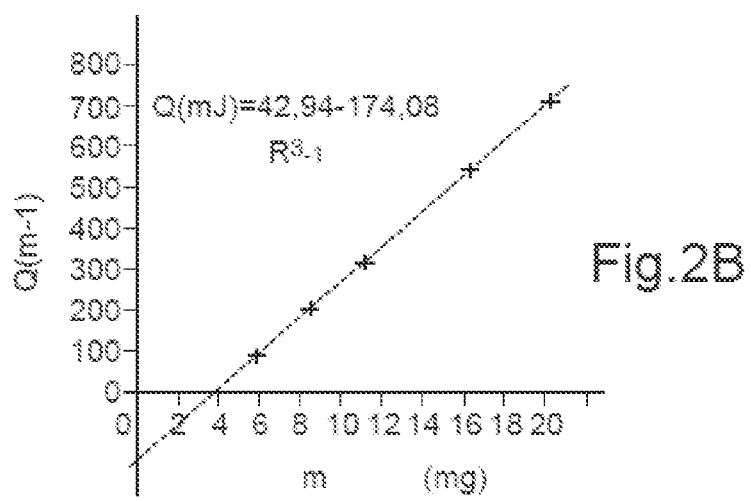
Figure 3:
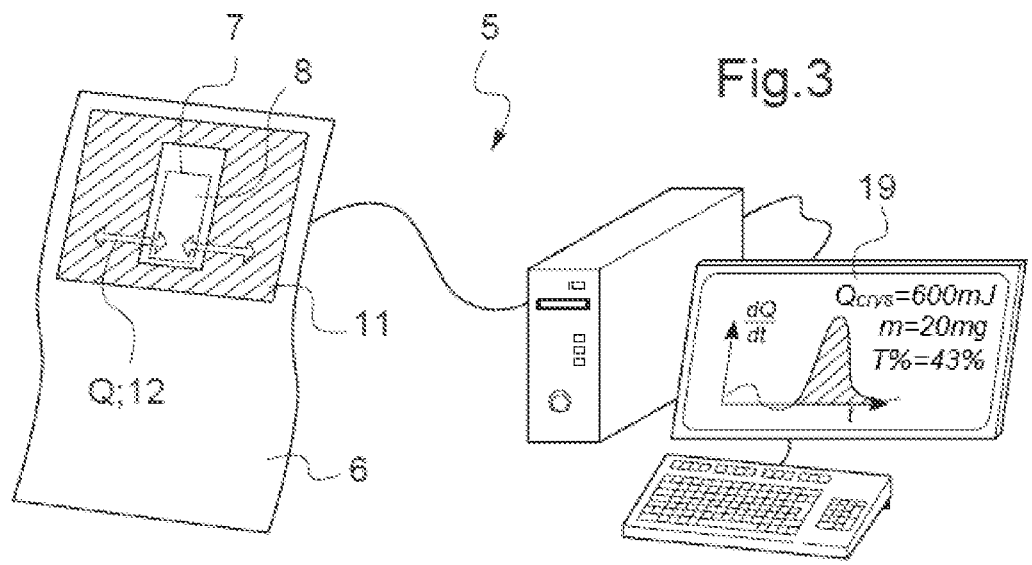
Figure 4:
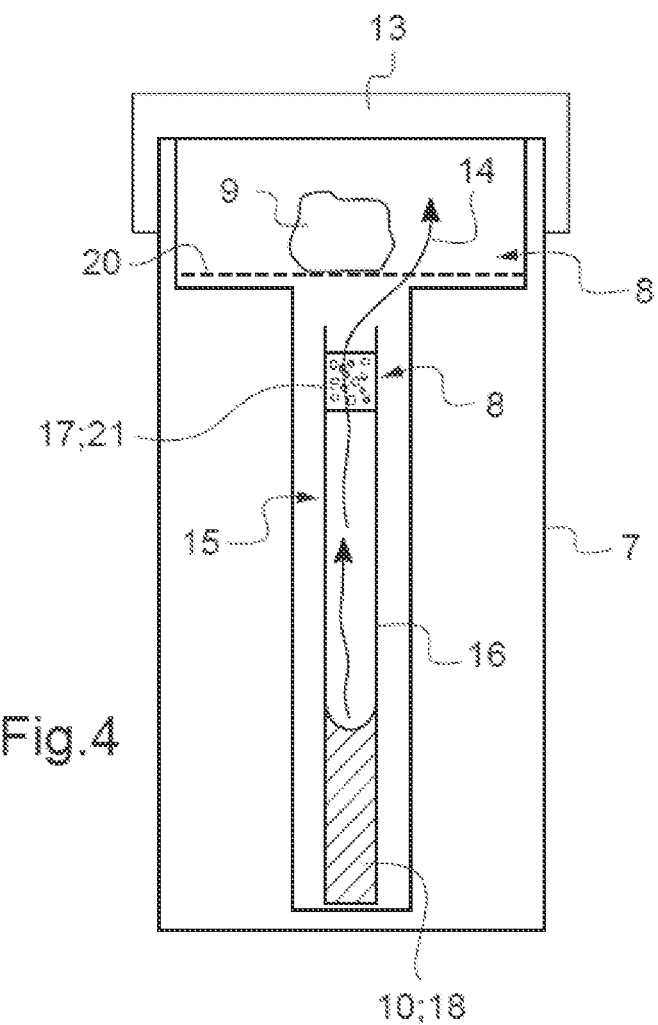
Figure 17:
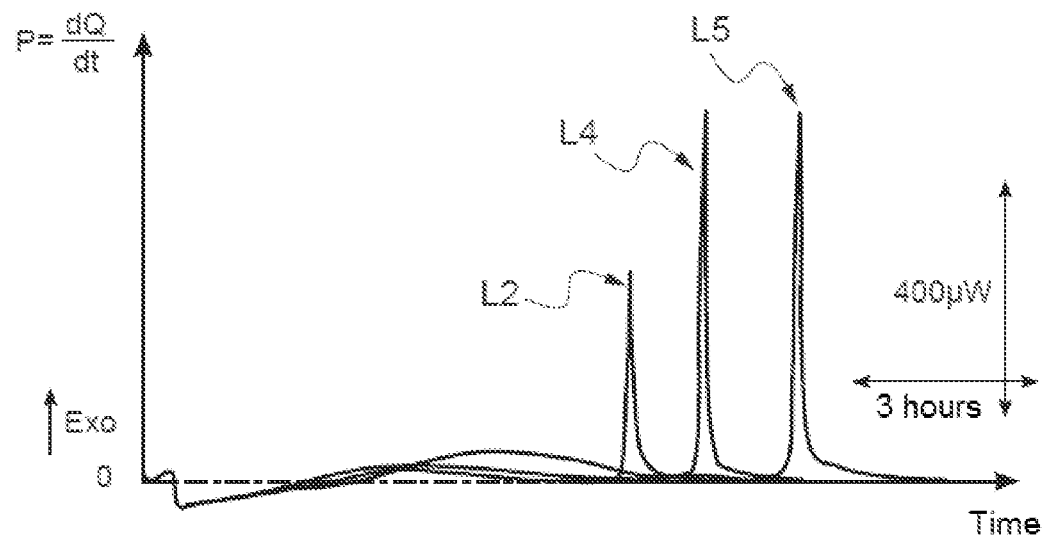
Figure 18:
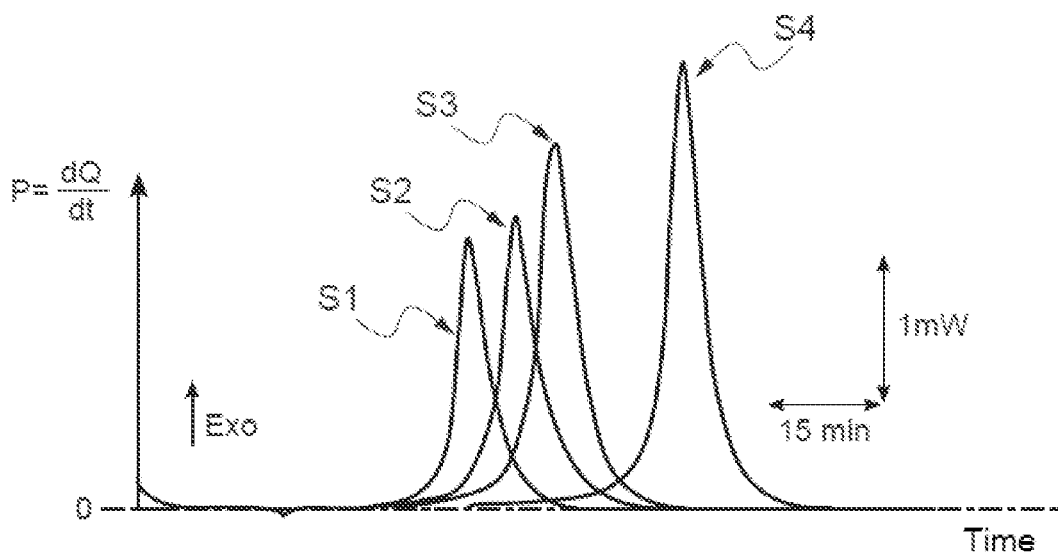
Figure 19:
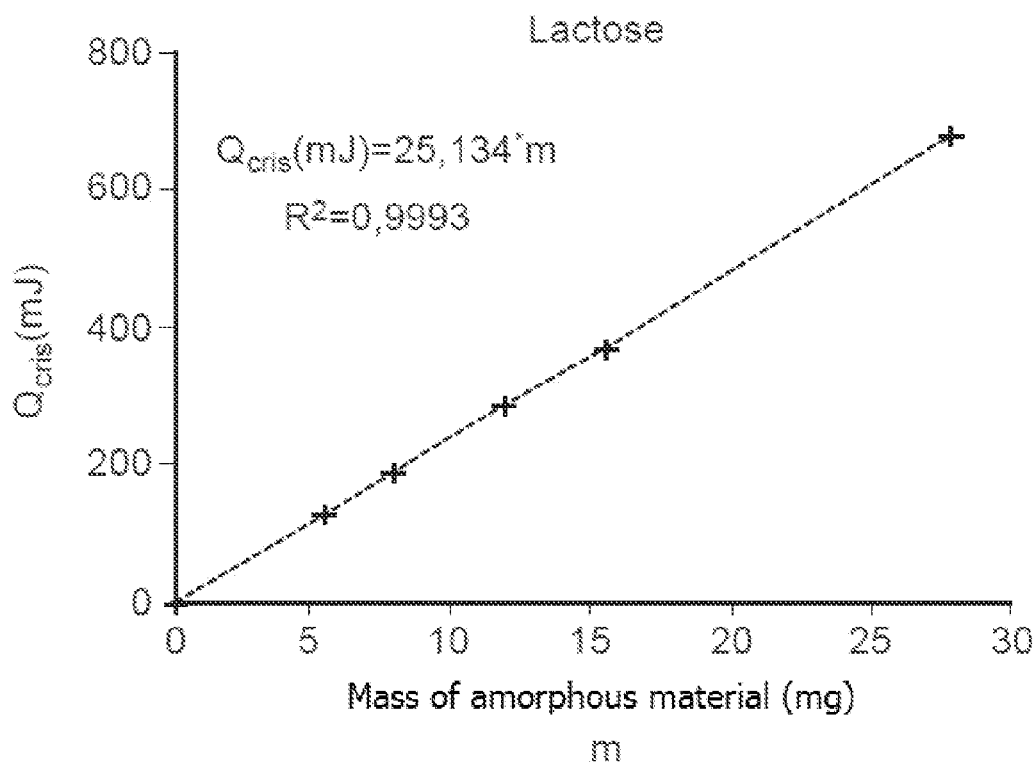
Figure 20:
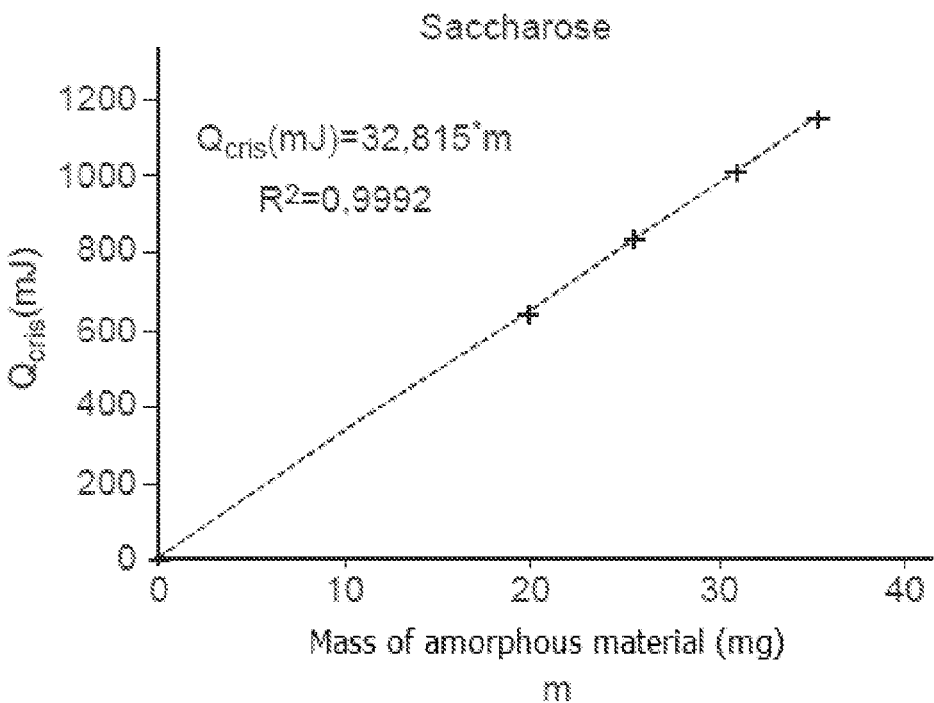
Figure 21:
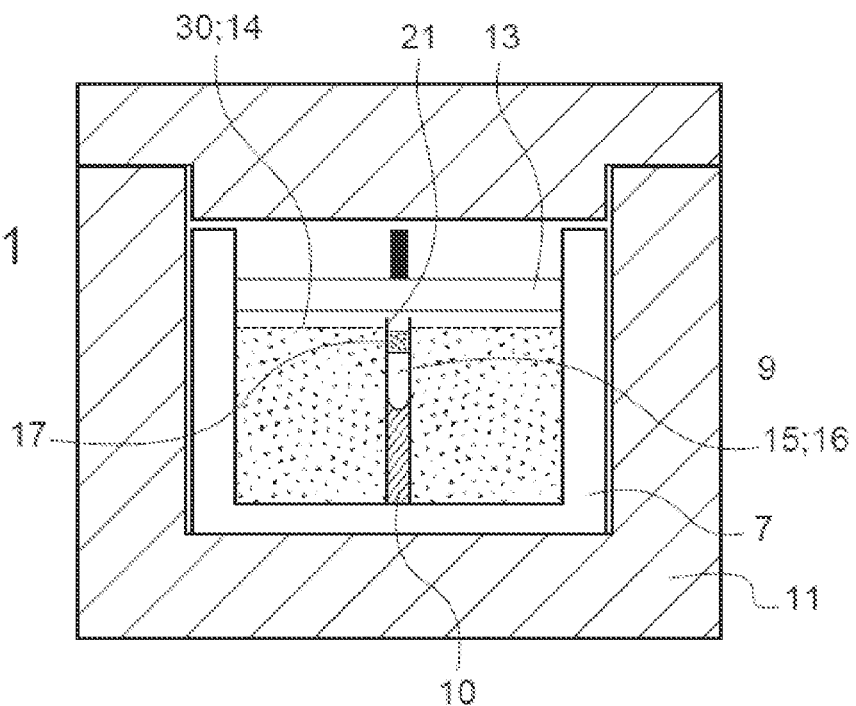
Figure 22:
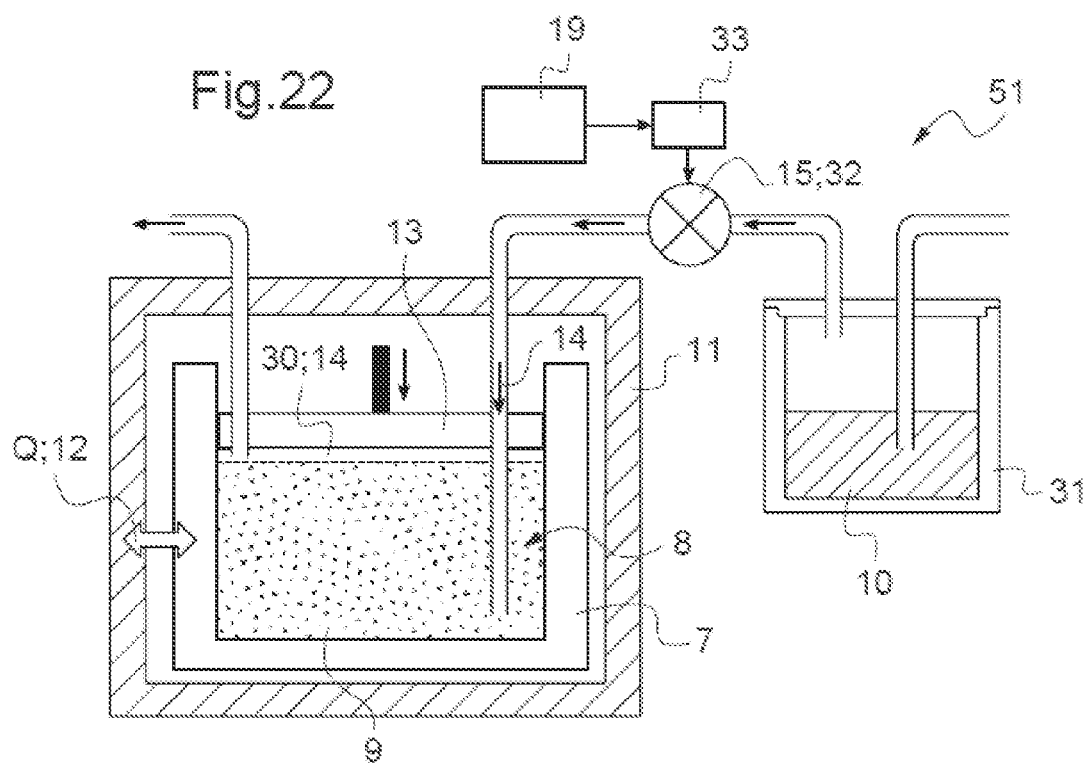
Figure 23:
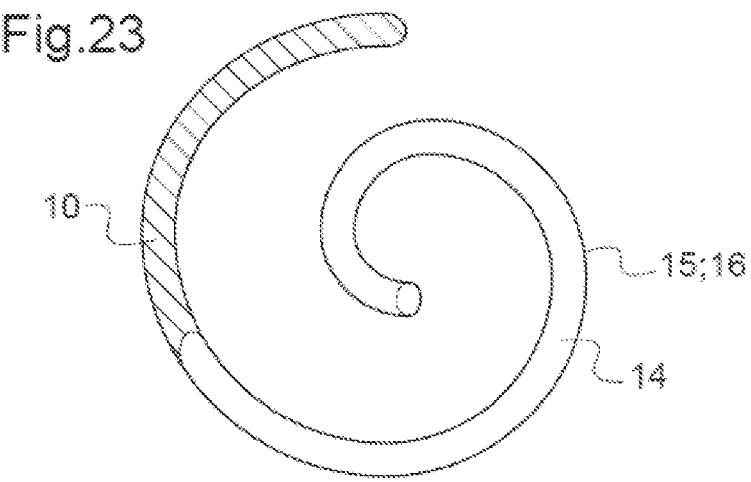
Figure 24:
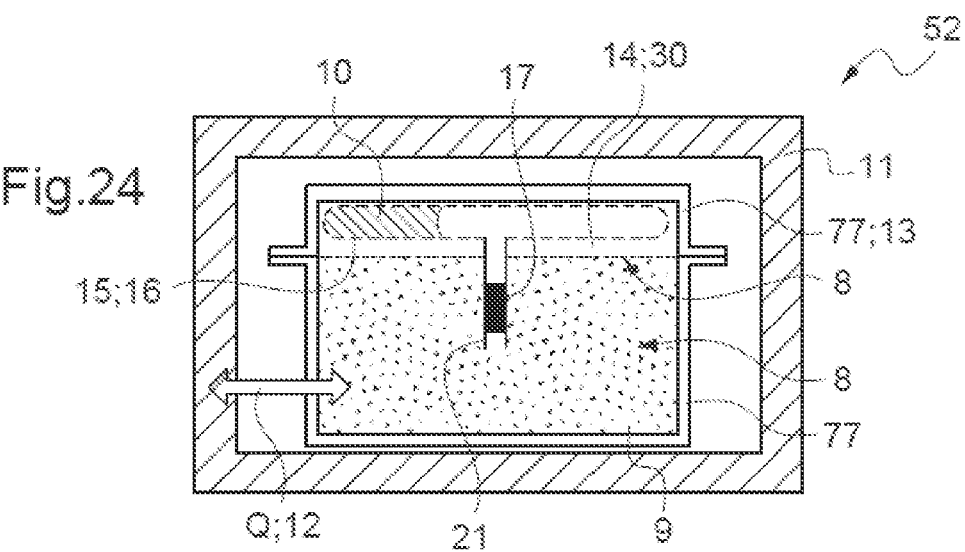
Figure 25:
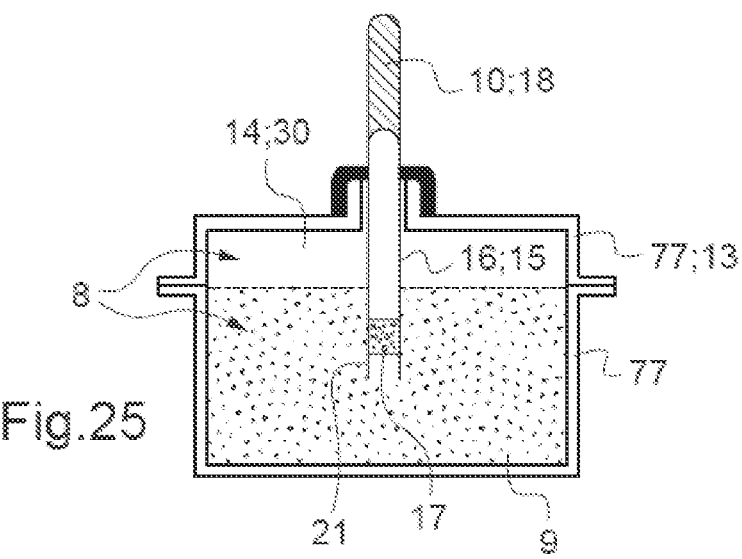

FIG. 2A shows thermal activity curves of three purely amorphous samples (sample 1, 3, 5), these curves being obtained according to the method of the prior art. The samples are amorphous lactose. The masses of the samples are respectively 5.9 mg (sample 1), 11.2 mg (sample 3) and 20.4 mg (sample 5). The heats of crystallization $Q_{crys}$ of each of the samples under the peaks "a", "b" and "c" are respectively 78.8 mJ (sample 1), 306.3 mJ (sample 3) and 701.0 mJ (sample 5);

FIG. 2B represents a calibration curve of a heat of crystallization $Q_{crys}$ of the purely amorphous sample of lactose as a function of the mass m of the sample of lactose, the heat $Q_{crys}$ being calculated according to the method of the prior art;

FIG. 3 diagrammatically represents a preferential embodiment of a device according to the invention;

FIG. 4 illustrates a first embodiment of a calorimetric ampoule in a closed system and made of glass for the device of FIG. 3;

FIG. 5 illustrates a second embodiment of a calorimetric ampoule in a closed system and made of glass for the device of FIG. 3;

FIG. 6 illustrates a third embodiment of a closed calorimetric ampoule made of glass for the device of FIG. 3;

FIGS. 7 to 11 are thermal activity curves of different partially amorphous samples, these curves being obtained by a first embodiment of the method according to the invention;

FIGS. 12 and 13 are thermal activity curves of different partially amorphous samples, these curves being obtained by a second embodiment of the method according to the invention;

FIGS. 14 and 15 are thermal activity curves of different partially amorphous samples, these curves being obtained by a second embodiment of the method according to the invention;

FIG. 16 illustrates thermal activity curves of different partially amorphous samples under vapour pressure of pure methanol or of methanol mixed with different proportions of glycerol. The peak 26a represents the heat of crystallization of 20.79 mg of sucrose under the vapour pressure of 100 μL of pure methanol. The peak 26b represents the heat of crystallization of 11.51 mg of sucrose under the vapour pressure of a solution of 100 μl of methanol in which glycerol is dissolved in a proportion of 1 g of methanol per 0.33 g of glycerol. The peak 26c represents the heat of crystallization of 11.37 mg of the sucrose under the vapour pressure of a solution of 100 μL of methanol in which glycerol is dissolved in a proportion of 1 g of methanol per 0.67 g of glycerol. The peak 26d represents the heat of crystallization of 11.52 mg of sucrose under the vapour pressure of a solution of 100 μL of methanol in which glycerol is dissolved in a proportion of 0.7 g of methanol per 0.9 g of glycerol;

FIGS. 17 and 18 illustrate different thermal activity curves of different purely amorphous samples, and FIGS. 19 and 20 represent calibration curves of a heat of crystallization $Q_{crys}$ of the samples of FIGS. 17 and 18 as a function of the mass m of these samples, the heat $Q_{crys}$ being crys calculated by a method according to the invention;

FIG. 21 illustrates a fourth embodiment of a calorimetric ampoule in a closed system and made of glass for the device of FIG. 3;

FIG. 22 illustrates a first variant of the device according to the invention in an open system for an isothermal calorimetry system;

FIG. 23 illustrates a first embodiment of a closed DSC pan for a second variant of the device according to the invention;

FIG. 24 illustrates a capillary in a spiral for the pan of FIG. 23;

FIG. 25 illustrates a second embodiment of the closed DSC pan for the second variant of the device according to the invention;

FIG. 26 illustrates a third variant of the device according to the invention in an open system for a DSC system;

FIGS. 27 to 32 illustrate different thermal activity curves of a sample, obtained by a method according to the invention.

Figure 1:
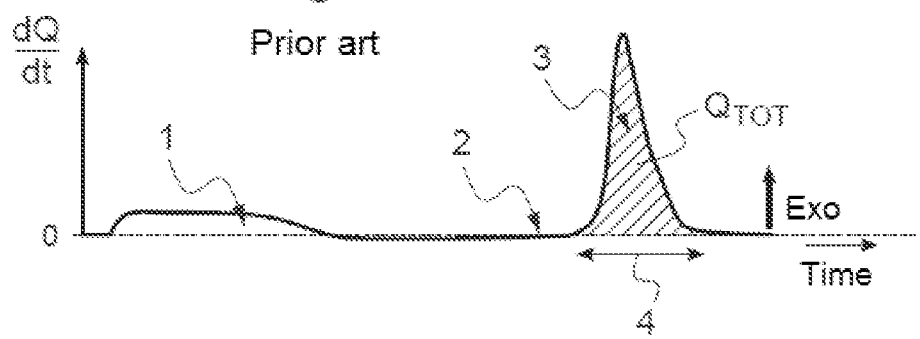
FIG. 1 illustrates a thermal activity curve according to the prior art.

With reference to FIGS. 1 and 2, the inventors commenced by demonstrating the lack of accuracy of a method for determining the mass m of amorphous material in a sample as described previously in the part entitled "prior art".

For this, the heat $Q_{crys}$ is measured several times in succession according to this method of the state of the art for different known amorphous masses m of lactose, and a calibration curve of this heat $Q_{crys}$ is established as a function of the increasing masses m. In the examples presented in FIG. 2A, the heat of crystallization $Q_{crys}$ represented by the peak "a" is obtained by integration of the area under the peak of crystallization "a" and is directly proportional to the mass m of the sample. The measurements are carried out at 25° C. The saturator controls the Relative Humidity at 38%. The saturated saline solution of the saturator is a solution of NaI. The linear regression line of the representation of the heat of crystallization $Q_{crys}$ as a function of the amorphous mass m of the sample is presented in FIG. 2B.

The linear regression gives a very good correlation coefficient $R^2=1$. The ordinate at the origin used for calculating the amorphous content should be zero. However, here it has a very high value and an atypical physical significance: for m less than 4 milligrams, the crystallization becomes endothermic!

According to the inventors of the present Patent Application, in the prior art, the inappropriate use of a saturated saline solution gives rise to significant and unacceptable biases for quantification of the mass m of amorphous material, as in this case the hypothesis according to which:
[the quantity of heat $Q_{tot}$ received or given up during the crystallization of the sample by the system comprising the sample and the saturated saline solution]
is equal to
[the heat of crystallization $Q_{crys}$ of the amorphous part of the sample]
is false.

A description will now be given, with reference to FIGS. 3 and 4, of a preferential embodiment of device 5 for controlling crystallization or recrystallization according to the invention, comprising a first embodiment of a closed calorimetric ampoule 7 made of glass.

The device 5 comprises a calorimeter 6. The calorimeter 6 is a microcalorimeter of the "TA Instruments 2277 Thermal Activity Monitor" type. The microcalorimeter 6 comprises a housing for the ampoule 7. The microcalorimeter 6, the housing and the ampoule 7 form means for receiving a system 8. The system 8 comprises the entire content of the ampoule, in particular a sample of solid material 9, a vapour source 10, and vapour 14. The ampoule 7 contains the sample of solid material 9 and the vapour source 10. The sample of solid material 9 is initially at least partially amorphous and/or at least partially crystalline when it is placed in the ampoule, i.e. before any crystallization or recrystallization of the sample 9 taking place within the device 5 and before any measurement implemented using the device 5. The vapour source 10 is a solution comprising at least one solvent for crystallizing said solid material 9, and is arranged for diffusing the vapour 14 from this at least one solvent in the ampoule 7. A solvent for crystallizing the solid material is a solvent which can initiate crystallization or recrystallization of this material. Typically, the crystallization or recrystallization is initiated in the case of a vapour pressure of this at least one solvent surrounding the solid material equal to or greater than a critical pressure Pc of crystallization or recrystallization.

The microcalorimeter 6 also comprises means 11 for stabilizing the temperature of the system 8, these means 11 surrounding the housing and the ampoule 7, these means 11 being arranged for cooling or reheating the system 8 until the system reaches an equilibrium temperature, the means 11 being moreover arranged to maintain the temperature of the system at this equilibrium temperature; thus, the microcalorimeter 6 is arranged so that the sample of material 9 and the vapour source 10 form an isothermal system 8, maintained at the equilibrium temperature. In order to maintain the temperature of the system 8 at the equilibrium temperature, the microcalorimeter 6 is arranged in order to exchange energy with the system 8 in the form of a quantity of heat Q (referenced 12), the microcalorimeter 6 giving up or receiving heat Q according to whether a respectively endothermic or exothermic reaction is taking place within the system 8. The means 11 typically comprise a Peltier effect module.

The means 11 are moreover arranged in order to continuously measure the quantity of heat Q, 12 or more precisely the heat flow $$P = \frac{dQ}{dt}$$

received or given up by the system 8.

Moreover, the ampoule 7 comprises a lid 13 for closing the system 8 inside the ampoule 7; thus, the microcalorimeter 6 is arranged so that the sample of material 9 and the vapour source 10 form a closed system 8, i.e. a system exchanging no material. The system 8 neither gives up nor receives any quantity of material.

The ampoule 7 of the microcalorimeter 6 is arranged so that the vapour 14 diffused by the source 10 comes into contact with the sample 9 and thus initiates crystallization or recrystallization of the sample 9.

The ampoule 7 also comprises means 15 for limiting a vapour diffusion rate 14 in the system 8, arranged so that the diffusion rate is less than 100 nano moles per second, preferably comprised between 1 pico mole per second and 1 nano mole per second of molecules of this vapour.

A limitation of the diffusion rate of the vapour 14 in the system 8 limits, reduces, checks, slows down or restrains the diffusion rate with respect to the case where the vapour source 10 would be situated in a large pan or beaker opening directly onto the sample 9.

The means 15 comprise a capillary 16 containing the vapour source 10. The diameter of the capillary is typically comprised between 1 micrometer and 1 millimeter. The sample 9 is placed on a grid 20, so as to be situated above the end 21 of the capillary 16 through which the vapour 14 leaves the capillary and is diffused. Thus, a capillary force holds said solvent in the capillary 16 and limits its diffusion in the system 8 around the sample.

The means 15 also comprise a stopper of material 17 situated at the end 21 of the capillary 16 through which the vapour 14 is diffused. The stopper 17 is a porous wall which separates the sample 9 and the part 18 of the capillary containing the vapour source 10, said wall 17 being arranged in order to limit the vapour diffusion 14 from the part 18 towards the sample of material 9. In other words, this wall 17 checks the passage of vapour of said solvent, from the capillary 16 towards the sample of material 9.

The means 15 are arranged so that the crystallization or recrystallization of the sample 9 commences only when the system 8 has reached the equilibrium temperature.

Finally, the device 5 also comprises calculation means 19 for calculating and determining a heat $Q_{crys}$ of crystallization or recrystallization and/or a mass of amorphous material m and/or an amorphous content T % of the sample 9, starting from a flow measurement $$P = \frac{dQ}{dt}$$

carried out by the measurement means. This determination is described in detail below for the description of the embodiments of the method according to the invention. The means 19 typically comprise a microprocessor, an analogue or digital electronic circuit or a computer, arranged in order to recover measurements originating from the measurement means 11 and for calculating and deducing $Q_{crys}$, m and T %. The means 19 also comprise means for displaying the $$\frac{dQ}{dt}$$

measurements originating from the measurement means 11, as well as the calculated data $Q_{crys}$ obtained from the means 19, m and T %.

In a variant of the first embodiment of an ampoule 7 of FIG. 4, the stopper 17 is a sealing stopper which, in a closed state, prevents the vapour 14 from leaving the capillary and, in an open state, allows the vapour 14 to leave the capillary and diffuse, the device 5 also comprising means for controlling the passage from the closed state to the open state, said passage being in particular controlled when the ampoule 7 is closed and when the system 8 has reached its equilibrium temperature.

In another variant of the first embodiment of an ampoule 7 of FIG. 4, the stopper 17 is not present.

A description will now be given, with reference to FIG. 5, of a second embodiment of a calorimetric ampoule in a closed system 7 and made of glass for the device 5 of FIG. 3.

This second embodiment of an ampoule is described only for its differences with respect to the first embodiment of an ampoule of FIG. 4.

In this second embodiment of an ampoule, the vapour source is not contained in a capillary 16. The second embodiment of an ampoule comprises two separate parts:

a first part 22 serving as a reservoir containing the vapour source 10, and a second part 23 comprising the sample of material 9.

The means of limitation of the diffusion rate 15 comprise a porous wall 24 separating the first 22 and the second 23 part (i.e. separating the sample 9 and the vapour source 10), said wall 24 being arranged in order to limit the vapour diffusion 14 from the reservoir 22 towards the sample of material 9. In other words, this wall 24 checks and limits the passage of vapour of said solvent, from the reservoir 22 towards the sample of material 9.

A description will now be given, with reference to FIG. 6, of a third embodiment of a closed calorimetric ampoule 7 made of glass for the device 5 of FIG. 3.

This third embodiment of an ampoule is described only for its differences with respect to the first embodiment of an ampoule of FIG. 4.

In this third embodiment of an ampoule, the vapour source 10 is not contained in a capillary 16. The means 15 of limitation of the diffusion rate comprise a support 25 which is not soluble in said solvent and in which the vapour source is absorbed. The support 25 is typically a polymer such as cellulose and its derivatives or glass wool, derivatives of silica or any product capable of containing the crystallization solvent and limiting its evaporation in a mechanical (porosity, tortuosity etc.) or physicochemical manner (diffusion). The nature of the above support is mentioned by way of example. Thus, forces of interaction between said solvent and the support 25 hold said solvent in the support and limit its diffusion into the system 8 around the sample 9. These forces of interaction typically include capillary forces exerted on said solvent by microcavities in the support in which said solvent is absorbed.

The third embodiment of an ampoule 7 comprises two separate parts:

a first part 22 serving as a reservoir containing the support 25 and the vapour source 10, and a second part 23 comprising the sample of material 9.

The means of limitation of the diffusion rate 15 also comprise a porous wall 24 separating the first 22 and the second 23 part (i.e. separating the sample 9 and the vapour source 10), said wall 24 being arranged in order to limit the vapour diffusion from the reservoir to the sample of material. In other words, this wall 24 checks the passage of vapour of said solvent, from the reservoir 22 to the sample of material 9.

In a variant of this third embodiment of an ampoule according to the invention, the wall 24 is not present.

A description will now be given, with reference to FIGS. 7 to 20, of different embodiments of the method according to the invention implemented by the device 5 comprising any one of the embodiments of an ampoule according to the invention previously described.

First, a description will be given of the points common to these different embodiments of the method according to the invention. In these different embodiments, the method for controlling crystallization or recrystallization according to the invention comprises:

a vapour diffusion 14 of said crystallization solvent in the closed isothermal system 8, said system 8 comprising the sample of solid material 9 and the vapour source 10 diffusing the vapour 14, the solid material 9 being initially at least partially amorphous and/or at least partially crystalline, crystallization (i.e. passage from an amorphous phase to a crystalline phase) or recrystallization (i.e. passage from one crystalline phase to another crystalline phase) of the sample 9 under the effect of the diffused vapour 14, at least during the crystallization or recrystallization, continuous measurement of heat received or given up by the system, the vapour source 10 comprising said solvent for crystallizing said solid material 9. The system 8 being isothermal, the crystallization or recrystallization and the measurement are carried out at a constant temperature, i.e. at the equilibrium temperature. During the crystallization or recrystallization respectively, the quantities of heat exchanged within the system other than the heat of crystallization or recrystallization of the sample are less than approximately 10%, in particular 5%, advantageously 1% of respectively the heat of crystallization or recrystallization of the sample. Of course, the quantities of heat exchanged within the system 8 excludes the quantities of heat exchanged between the system 8 and its outer environment, such as for example the quantity of heat Q exchanged between the system 8 and the means 11. This condition is not achieved by the prior art.

In other words, the vapour source 10 in the closed isothermal system 8 is used to control the crystallization or recrystallization of the sample of solid material 9, which is initially at least partially amorphous and/or at least partially crystalline, contained in the closed system 8, said vapour source 10 comprising said solvent for crystallizing said solid material, the vapour diffusion of which leads to the crystallization or recrystallization of the sample, said vapour source 10 being such that the quantities of heat exchanged within the system during respectively the crystallization or recrystallization of the sample other than respectively the heat of crystallization or recrystallization of the sample are less than approximately 10%, in particular 5%, advantageously 1% of respectively the heat of crystallization or recrystallization of the sample.

Particular Case of a Crystallization

The more particular case of a crystallization will now be considered. The sample of material 9 initially comprises an amorphous and crystalline mixture. The sample has a total amorphous and crystalline mass M, including a mass m of amorphous material. The mass M of the sample is known. The sample of material 9 is a solid, in a single block or in powder form. The sample of material 9 typically comprises lactose, sucrose, salbutamol or a mixture thereof. The sample of material 9 is placed in the ampoule 7 with the vapour source 10. After closing the ampoule 7, the ampoule is placed in the microcalorimeter 6.

Once the ampoule is placed in the microcalorimeter 6, the means 11 are used for cooling down or raising the temperature of the system 8 until the system 8 reaches an equilibrium temperature, and for maintaining the system at this equilibrium temperature during the measurements to be carried out. The time taken to reach the equilibrium temperature is typically 30 minutes.

Moreover, once the ampoule is placed in the microcalorimeter 6, the vapour diffusion 14 commences. The vapour pressure of said solvent increases in the system 8 (i.e. in the ampoule), until the critical pressure of crystallization Pc is reached. Once the critical pressure of crystallization Pc is reached, the crystallization of the sample 9 commences. After reaching the critical pressure of crystallization Pc, the vapour pressure of said solvent can optionally continue to increase. The diffusion comprises a vapour diffusion of said crystallization solvent:
- contained in the capillary 16, the diffusion optionally passing through the stopper 17 if it is present, or
- absorbed in the support 25 which is not soluble in this at least one solvent, or
- contained in the reservoir 22 and separated from the sample 9 by the porous wall 24, according to the embodiment of an ampoule 7 according to the invention used.

The capillary 16, the stopper 17, the support 25 and the wall 24 ensure limitation of the vapour diffusion rate 14 in the system 8.

The limitation of the diffusion rate is arranged so that the crystallization of the sample 9 commences only when the system has reached the equilibrium temperature. In other words, the limitation of the diffusion rate is arranged so that the system 8 reaches the equilibrium temperature before reaching the critical pressure of crystallization Pc of said solvent starting from which the crystallization of the sample 9 commences.

After the system has reached the equilibrium temperature and at least during the crystallization of the sample 9, the means 11 continuously measure the quantity of heat Q received or given up by the system 8 within the microcalorimeter 6. More precisely, the heat flow $$P = \frac{dQ}{dt}$$

exchanged by the system 8 is measured continuously over time, this heat flow being equal to the derivative of Q as a function of time t. This heat flow represents the thermal activity of the system 8. The monitoring and recording of P as a function of time provides thermodynamic and kinetic information on the crystallization of the sample 9. On the curve representing P as a function of the time, a peak 26 of the thermal activity P is observed, which lasts for a time interval 27.

Then, the means 19 calculate and determine the heat of crystallization $Q_{crys}$ of the sample 9. Because the quantities of heat exchanged within the system during the crystallization of the sample other than the heat of crystallization of the sample are less than approximately 10%, in particular 5%, advantageously 1% of the heat of crystallization of the sample, the following calculation method becomes realistic: $Q_{crys}$ is calculated by considering that it is equal to $Q_{tot}$, the integral of the thermal activity $$P = \frac{dQ}{dt}$$

over the time interval 27 of the peak 26.

Then, the means 19 calculate and determine the mass of amorphous material m in the sample according to the following formula:

$$m = \frac{Q_{crys}}{\Delta H_{crys}}$$

Where $\Delta H_{crys}$ is the enthalpy of crystallization of the amorphous material in the sample 9. The material of the sample 9 being known, $\Delta H_{crys}$ is measured beforehand on a known amorphous mass of the material to be analyzed (this known mass of amorphous material is prepared by lyophilization), known because $\Delta H_{crys}$ depends on the material composing the sample 9.

Thus, the means 19 calculate and determine the level T % of amorphous material in the sample 9 according to the following formula:

$$T\% = \frac{m}{M} \text{ with } 0 < T\% < 1$$

First Embodiment of the Method According to the Invention

According to a first embodiment of the method according to the invention, said solvent in the vapour source 10 comprises no dissolved solute. In particular, said solvent in the vapour source comprises no dissolved salt. The vapour source comprises said solvent, but comprises no solute dissolved in said solvent. This is a preferential embodiment in order that the quantities of heat exchanged within the system 8 during the (re)crystallization of the sample other than the heat of (re)crystallization of the sample are less than approximately 10%, in particular 5%, advantageously 1% of the heat of (re)crystallization of the sample.

In a first variant of the first embodiment of the method according to the invention, the vapour source is a single pure solvent, preferably selected from pure water or an organic solvent such as methanol or ethanol. By pure solvent is meant a solvent in which no solute is dissolved.

In a second variant of the first embodiment of the method according to the invention, the vapour source is a mixture of solvents preferably selected from pure water or an organic solvent such as methanol or ethanol, in particular the "methanol-ethanol" or "water-ethanol" or also "water-methanol"

mixture. The vapour source 10, i.e. the mixture of solvents, comprises no dissolved solute.

FIG. 7 represents the thermal activity curve $$P = \frac{dQ}{dt}$$

obtained by the device 5 with the first embodiment of an ampoule 7 of FIG. 4, for an equilibrium temperature of 25° C., the sample 9 being lactose, the vapour source 10 being a solution of pure methanol. The means 19 calculate:

m=15.09 mg.

FIG. 8 represents the thermal activity curve $$P = \frac{dQ}{dt}$$

obtained by the device 5 with the first embodiment of an ampoule 7 of FIG. 4, for an equilibrium temperature of 25° C., the sample 9 being lyophilized lactose, the vapour source 10 being pure water. The means 19 calculate:

m=3.64 mg.

FIG. 9 represents the thermal activity curve $$P = \frac{dQ}{dt}$$

obtained by the device 5 with the first embodiment of an ampoule 7 of FIG. 4, for an equilibrium temperature of 25° C., the sample 9 being lyophilized lactose, the vapour source 10 being a mixture of methanol and ethanol according to a 50%-50% ratio. The means 19 calculate:

m=4.35 mg.

FIG. 10 represents the thermal activity curve $$P = \frac{dQ}{dt}$$

obtained by the device 5 with the first embodiment of an ampoule 7 of FIG. 4, for an equilibrium temperature of 25° C., the sample 9 being lyophilized lactose, the vapour source 10 being a mixture of water and ethanol according to a 70% water-30% ethanol ratio. The means 19 calculate:

m=4.49 mg.

FIG. 11 represents the thermal activity curve $$P = \frac{dQ}{dt}$$

obtained by the device 5 with the first embodiment of an ampoule 7 of FIG. 4, for an equilibrium temperature of 25° C., the sample 9 being a mixture of lyophilized lactose and lyophilized sucrose, the vapour source 10 being a solution of pure methanol. It is known that sucrose crystallizes before lactose. The means 19 reiterate the calculations of $Q_{crys}$ and m for each of the peaks 28, 29 corresponding to the crystallization of the sucrose and of the lactose respectively. The means 19 calculate a mass of amorphous sucrose m(sucrose)=11.66 mg. The means 19 calculate a mass of amorphous lactose m(lactose)=5.50 mg.

For each of the cases of FIGS. 7 to 9, the means 19 calculate the amorphous lactose (and optionally sucrose) content T % according to the formula:

$$T\% = \frac{m}{M}$$

where M is the total mass of the sample 9.

Second Embodiment of the Method According to the Invention

According to a second embodiment of the method according to the invention, the vapour source comprises a solute dissolved in said crystallization solvent.

In a first variant of the second embodiment of the method according to the invention, said solute is in a quantity less than the quantity necessary for the saturation of the solute in said solvent. Solute-solvent mixtures may be mentioned below as non-exhaustive examples: sucrose-methanol, sucrose-ethanol, lactose-methanol, lactose-ethanol, methanol glycerol, making it possible to fix the activity of the crystallization solvent at the value of the vapour pressure of crystallization of the amorphous material. FIG. 16 shows examples with methanol-glycerol mixtures at different ratios. Here the glycerol is a solute and not a solvent, as its vapour pressure is too low to crystallize the amorphous material.

FIG. 12 illustrates the first variant of the second embodiment of the method according to the invention. FIG. 12 represents the thermal activity curve $$P = \frac{dQ}{dt}$$

obtained by the device 5 with the first embodiment of an ampoule 7 of FIG. 4, for an equilibrium temperature of 25° C., the sample 9 being lyophilized sucrose, the vapour source 10 being a solution of methanol in which glycerol is dissolved in a proportion of 0.7 g of methanol per 0.9 g of glycerol. The means 19 calculate:

m=11.52 mg.

In a second variant of the second embodiment of the method according to the invention, the solute is at saturation in said solvent, but the solute dissolved in said solvent has a crystallization latency time greater than a latency time respectively of crystallization or recrystallization of the sample such that the solute only crystallizes in the vapour source after the end respectively of the crystallization or recrystallization of sample 9.

FIG. 13 illustrates the second variant of the second embodiment of the method according to the invention. FIG. 13 represents the thermal activity curve $$P = \frac{dQ}{dt}$$

obtained by the device 5 with the first embodiment of an ampoule 7 of FIG. 4, for an equilibrium temperature of 25° C., the sample 9 being lyophilized sucrose, the vapour source 10 being a methanol solution saturated with sucrose at 4° C. and filtered. The means 19 calculate:

m=23.18 mg.

FIG. 14 illustrates the second variant of the second embodiment of the method according to the invention. FIG. 14 represents the thermal activity curve $$P = \frac{dQ}{dt}$$

obtained by the device 5 with the first embodiment of an ampoule 7 of FIG. 4, for an equilibrium temperature of 25° C., the sample 9 being amorphous lactose, the vapour source 10 being a methanol solution saturated with lactose at 4° C. The means 19 calculate:

m=32.96 mg

FIG. 15 also illustrates the second variant of the second embodiment of the method according to the invention. FIG. 15 represents the thermal activity curve $$P = \frac{dQ}{dt}$$

obtained by the device 5 with the first embodiment of an ampoule 7 of FIG. 4, for an equilibrium temperature of 25° C., the sample 9 being amorphous sucrose, the vapour source 10 being a methanol solution saturated with lactose at 4° C.

m=15.35 mg

In fact, if the vapour source 10 becomes supersaturated with solute following the evaporation of said solvent but is kinetically stable, i.e. it does not crystallize rapidly, the crystallization of the solute will occur after the crystallization or recrystallization of the sample and will not disturb the measurement of the thermal activity $$P = \frac{dQ}{dt}.$$

In a third variant of the second embodiment of the method according to the inventions, the solute exhibits no heat of solvation in said solvent, i.e. it exhibits no heat of hydration and no heat of dissolution in said solvent. This embodiment can be also combined with the first or second variant of the second embodiment.

Comments on the Means 15 for Limiting the Diffusion Rate of the Vapour 14

The means 15 are not absolutely necessary for implementing a method according to the invention, but they are particularly advantageous.

Compared with a use of a saturated saline solution according to the prior art, the use according to the invention of a pure solvent or of a solvent mixture without dissolved solute will impose a saturating partial pressure in the ampoule 7, which will significantly speed up the hydration phase of the amorphous part of the sample 9 and risks leading to too rapid a crystallization or recrystallization of the sample 9 which can take place during the placing of the sample or also during its thermal equilibrium (30 minutes) before measurement. This risk is significant for amorphous materials with a high hydration rate such as salbutamol. Rather than shortening the thermal equilibrium time of the sample 9 to five minutes instead of the half-hour required (which would introduce other measurement artefacts linked to the difference in temperature between the sample 9 not at equilibrium and the microcalorimeter bath), the means 15 make it possible to ensure that the crystallization or recrystallization of the sample 9 commences only after the stabilization of the sample at the equilibrium temperature.

The means 15 make it possible to control the diffusion of the vapour 14 of said crystallization solvent, in order to ensure a slow and managed increase in the vapour pressure within the ampoule 7 and to reach the critical vapour pressure of crystallization or recrystallization Pc of the sample 9 within a reasonable length of time.

When the a vapour source 10 comprising a saturated or unsaturated solute is used, the adoption of the means 15 is particularly important not only to control the diffusion of the vapour 14 of said crystallization solvent, but also for allowing the solute dissolved in said solvent to have a crystallization latency time greater than a crystallization or recrystallization latency time of the sample such that the solute crystallizes only after the end of crystallization or recrystallization of the sample.

Demonstration of the Accuracy of the Method According to the Invention.

In order to verify the accuracy of the method according to the invention, calibration curves of $Q_{crys}$ as a function of m are produced in the case where the sample 9 is 100% amorphous lactose (m=M) and in the case where the sample 9 is 100% amorphous sucrose (m=M).

The mass m of each of the samples is therefore known.

The vapour source 10 is a solution of pure methanol.

The amorphous lactose and sucrose are obtained by lyophilization of an aqueous solution at 10%. The lyophilizates are placed in a desiccator under 0% relative humidity (RH) and under vacuum. Samples 9 are taken then weighed under 0% relative humidity and placed to crystallize at 25° C. within the microcalorimeter 6 of the device 5 with the first embodiment of an ampoule 7 of FIG. 4.

The samples are placed in 4 ml calorimetric ampoules 7 made of glass. The vapour pressure of the methanol is controlled by the capillary 16 (with a diameter slightly less than 1 mm). The sample 9 is weighed directly in the ampoule. Once the source 10 has been added to the capillary 16, the sample 9 is introduced into the microcalorimeter 6 (TA Instruments 2277 Thermal Activity Monitor). It remains in equilibrium position for 30 minutes in order to reach its equilibrium temperature (25° C.) then it is lowered into the measurement position and the thermal traces $$P = \frac{dQ}{dt}$$

are recorded.

Examples of the thermal activity $$P = \frac{dQ}{dt}$$

of lactose and of sucrose are respectively presented in FIGS. 17 and 18. Table 1 below gives:
  the identification of the sample (S1 to S4, or L1 to L6),
  the nature of the material composing the sample (lactose or sucrose),
  the mass m of each of the samples, and
  the heat of crystallization $Q_{crys}$ each of the samples, obtained after integration of $$P = \frac{dQ}{dt}$$

under the peak of crystallization of each of the samples as explained previously.

The crystallization of the amorphous lactose and sucrose is clearly observed on the thermal traces recorded.

The crystallization induction times are sufficiently long (approximately 6 hours for lactose and 30 minutes for sucrose) and make it possible to visualize the crystallization in the measurement time.

TABLE 1

| Sample | Nature | mass m (mg) with m = M | Heat of crystallization $Q_{crys}$ (mJ) |
|---|---|---|---|
| L1 | Lactose | 5.13 | 128.3 |
| L2 | Lactose | 7.50 | 181.1 |
| L3 | Lactose | 7.81 | 193.0 |
| L4 | Lactose | 11.5 | 292.8 |
| L5 | Lactose | 15.09 | 369.8 |
| L6 | Lactose | 27.22 | 690.9 |
| S1 | Sucrose | 19.81 | 633.7 |
| S2 | Sucrose | 25.64 | 829.2 |
| S3 | Sucrose | 30.41 | 1008.4 |
| S4 | Sucrose | 34.78 | 1150.4 |

The crystallization peaks obtained are narrow, perfectly integrable and exhibit no shoulder. The calibration curves representing the heats of crystallization of the amorphous lactose and sucrose as a function of the quantity of amorphous material as well as their linear regressions, are illustrated in FIGS. 19 and 20 respectively.

The enthalpy of crystallization $\Delta H_{crys}$ of lactose under a methanol atmosphere is $-25.1 \pm 0.5$ J/g and $-32.8 \pm 0.6$ J/g in the case of sucrose. The linear regression of the curve in the form $Q_{crys} = a \cdot m + b$ gives a value of the ordinate at the origin of $-3.96$ for lactose (as against $-174.08$ for lactose crystallized with saturated saline solutions, see FIG. 2) and $-7.72$ for sucrose. These are low and it is possible to measure a mass of amorphous material by this method up to 0.25 mg.

Of course, the invention is not limited to the examples which have just been described and numerous adjustments can be made to these examples without exceeding the scope of the invention.

In variants of the embodiments of the method according to the invention previously described, the sample of material 9 can comprise an initially polymorphic or pseudo-polymorphic crystal, and instead of crystallization of the sample 9 (i.e. passage of all or part of the sample from an amorphous phase to a crystalline phase), there is recrystallization of the sample comprising passage from a crystalline phase to another crystalline phase of part or all of the sample, the method according to the invention then comprising a determination, by the means 19, and according to the same method of calculation as that previously described:

of a quantity of heat of recrystallization $Q_{crys}$ by integration of the thermal activity $$P = \frac{dQ}{dt}$$

over a time interval corresponding to the duration of a recrystallization peak 26, of the mass m of one of the crystalline phases and of a level T % of this crystalline phase with respect to the total mass M of the sample, $\Delta H_{crys}$ corresponding to an enthalpy of recrystallization.

Thus, the sample can initially be a pure crystal.

In other variants of the embodiments of the method according to the invention previously described, the sample can initially (i.e. before the commencement of the crystallization) be a pure amorphous material. In this case, the method according to the invention can be reiterated with numerous different experimental conditions (equilibrium temperature, nature of said solvent), so as to optimize the crystallization of the sample of material considered, as a function of the measurements of $$P = \frac{dQ}{dt}$$

and of the heats $Q_{crys}$ calculated. Clearly, the mass m is not calculated in this case.

A description will now be given, with reference to FIG. 21, of a fourth embodiment of a closed calorimetric ampoule 7 made of glass for the device of FIG. 3, for implementing a variant of any one of the embodiments of the method according to the invention previously described. This fourth embodiment of a calorimetric ampoule is described only for its differences with respect to the ampoule of FIG. 4.

In this variant, a sample 9 which is in powder form is used. The capillary 16 is placed in the ampoule 7 so that its end 21 is just proud of the sample 9 and opens into the free internal volume 30 of the ampoule not occupied by the sample 9. Throughout this document, by free internal volume 30 (or dead volume) is meant the entire volume situated inside the ampoule 7 in which the vapour 14 and only the vapour 14 can be accommodated. In FIG. 21, this free volume 30 is equal to the total internal volume of the ampoule 7 minus the volume of the powder 9 and minus the volume of the capillary 16.

The lid 13 is a piston arranged to be lowered in order to adjust the total internal volume of the ampoule 7. This piston 13 is lowered so that the free internal volume 30 of the ampoule, also called the dead volume, is less than 5% of the volume of the sample 9. This condition is particularly important for the closed system and makes it possible, in the implementation of a method according to the invention, to significantly reduce the exchanges between the molecules (for example of water) of the vapour phase 14 and the molecules (for example of water) expelled by the sample 9 during the crystallization.

A description will now be given, with reference to FIG. 22, of a first variant of a device 51 according to the invention in an open system for implementing a variant of any one of the embodiments of the method according to the invention previously described. FIG. 22 does not show the device 51, but only these differences with respect to the device of FIG. 3. This first variant of a device 51 according to the invention in an open system is described only for its differences with respect to the device of FIG. 3.

In this variant, the vapour source 10 is situated outside the system 8, in a container 31.

In this variant, the lid 13 is pierced so that the system 8 is not enclosed inside the ampoule; thus, the calorimeter 6 is arranged so that the sample of material 9 forms a open system 8, i.e. a system exchanging material. The system 8 gives up the quantity of material to, and receives it from the outside of the ampoule.

The means 15 comprise no stopper 17 but comprise a pump 32 situated outside the calorimeter, linking the container 31 to the system 8, and arranged for controlling and managing the vapour diffusion rate 14. The pump is arranged for injecting a carrier gas (such as air or nitrogen) saturated with the vapour 14 of the at least one crystallization solvent. The pump is arranged so that the diffusion rate of the vapour 14 is less than 100 nano moles per second, preferably comprised between 1 pico mole per second and 1 nano mole per second of the molecules of this vapour.

The device 51 also comprises means 33 of control of the pump arranged for adjusting the diffusion rate of the vapour 14 as a function of the response of the sample 9 (i.e. of the quantity of heat measured) during the hydration phase. More particularly, the means of control of the pump are arranged in order to commence the hydration phase with a high diffusion rate, then to reduce the diffusion rate over time so as not to cause crystallization during the hydration phase. Thus, the analysis time is reduced by speeding up the hydration phase while preventing crystallization during the hydration phase.

Moreover, the lid 13 is a piston arranged to be lowered in order to adjust the total internal volume of the ampoule 7. This piston 13 is lowered so that the free internal volume 30 of the ampoule, also called the dead volume, is less than 5% of the volume of the sample 9. Thus, the exchanges between the molecules (for example of water) of the vapour phase 14 and the molecules (for example of water) expelled by the sample 9 are significantly reduced during crystallization.

Finally, the pump is arranged in order to inject the vapour 14 directly inside the sample 9 in powder form, which makes it possible to improve the crystallization of the sample.

A description will now be given, with reference to FIGS. 23 and 24, of a first embodiment of a closed DSC pan for a second variant 52 of a device according to the invention implementing a variant of any one of the embodiments of the method according to the invention previously described. This second variant of a device 52 according to the invention in an open system is described only for its differences with respect to the device of FIG. 3. FIG. 23 does not show all of the device 52, but only these differences with respect to the device of FIG. 3.

Instead of the closed calorimetric ampoule 7 made of glass, the device 52 comprises a pan 77 of a DSC device.

In the device 52, the calorimeter 6 is not a microcalorimeter but a differential scanning calorimetry (DSC) device which comprises a housing for the DSC pan 77, but which is used in isothermal measurement mode.

Only the sensors of the differential scanning calorimetry (DSC) device are used, not its thermal energy. Thus, the DSC is changed from its first use, or an additional function is added to this apparatus: the phenomena of crystallization induced by controlled low-speed vapour scanning, i.e. by scanning under pressure, are measured. The operation is therefore carried out under isothermal conditions. Thus:

1) any DSC sample pan is used, as its volume is reduced with respect to that of a calorimetric cell (100 µl as against 3 ml minimum for calorimetry).
2) the thermal regulation of the furnace of this same DSC is used in order to maintain our sample at a constant temperature (25° C. in this case).
3) the sensors of this same DSC are used in order to measure the heat flow, as they produce results as good as those of microcalorimetry sensors (in terms of Joules measured per mass of the sample).
4) the system for recording and visualizing data from this same DSC is used, since although all commercial DSC software allows representation of the thermal power as a function of temperature, it also allows the representation of this same thermal power as a function of time as isothermal calorimetry. The temperature scanning function is therefore not used.
5) The control of the humidity and the vapour diffusion rate are added (as will be seen hereafter, either in closed pan preferably containing a sample with a capillary in a spiral acting as the so-called nanohygrostat vapour source, or in an open pan preferably with the vapour source outside the system equipped with a pump in order to ensure a controlled and low flow rate of the vapour in the sample).
5) the software of this same DSC is used in order to obtain the area under the curve of crystallization and to print the results.

A DSC is therefore used as apparatus (except for its temperature scanning function) with the added function of scanning with controlled low-speed vapour pressures in a closed or open pan, here for the purpose of measuring crystallization induced by the vapour.

Of course, according to the invention, this new function added to the DSC as apparatus can also be used in fields other than crystallization, whenever control of the rate (and/or of its variation) of introduction of molecules into the vapour state induces a physical, chemical or biological reaction in the sample, which can be measured by monitoring the heat flow that it generates.

The calorimeter 6, the housing and the pan 77 form means for receiving the system 8. The system 8 comprises all the content of the pan 77, in particular the sample of solid material 9 which is in powder form, the vapour source 10, and the vapour 14 as previously described. The pan 77 contains the sample of solid material 9 and the vapour source 10. The sample of solid material 9 is initially at least partially amorphous and/or at least partially crystalline when it is placed in the pan, i.e. before any crystallization or recrystallization of the sample 9 taking place within the device 52 and before any measurement implemented by means of the device 52. The vapour source 10 is a solution comprising at least one solvent for crystallizing said solid material 9, and is arranged in order to diffuse vapour 14 from this at least one solvent in the pan. A solvent for crystallizing the solid material is a solvent which can initiate crystallization or recrystallization of this material. Typically, the crystallization or recrystallization is initiated for a vapour pressure of this at least one solvent surrounding the solid material equal to or greater than a critical pressure Pc of crystallization or recrystallization.

The calorimeter 6 also comprises the means 11 of stabilization of the temperature of the system 8 described previously, these means 11 surrounding the housing and the pan, these means 11 being arranged in order to cool down or heat the system 8 until the system reaches an equilibrium temperature, the means 11 being moreover arranged in order to maintain the temperature of the system at this equilibrium temperature; thus, the calorimeter 6 is arranged so that the sample of material 9 and the vapour source 10 form an isothermal system 8, maintained at the equilibrium temperature. In order to maintain the temperature of the system 8 at the equilibrium temperature, the calorimeter 6 is arranged in order to exchange with the system 8 energy in the form of a quantity of heat Q (referenced 12), the calorimeter 6 giving up or receiving heat Q according to whether a respectively endothermic or exothermic reaction is taking place within the system 8. The means 11 include typically a Peltier effect module.

The means 11 are moreover arranged in order to continuously measure the quantity of heat Q, 12 or more precisely the heat flow $$P = \frac{dQ}{dt}$$

received or given up by the system 8.

Moreover, the pan 77 comprises a lid 13 for closing the system 8 inside the pan; thus, the calorimeter 6 is arranged so that the sample of material 9 and the vapour source 10 form a closed system 8, i.e. a system exchanging no material. The system 8 neither gives up nor receives any quantity of material.

The pan of the calorimeter 6 is arranged so that the vapour 14 diffused by the source 10 comes into contact with the sample 9 and thus initiates crystallization or recrystallization of the sample 9.

The pan also comprises means 15 for limiting a vapour diffusion rate 14 in the system 8.

A limitation of the diffusion rate of the vapour 14 in the system 8 limits, reduces, checks, slows down or restrains the diffusion rate with respect to the case where the vapour source 10 would be situated in a large pan or beaker opening directly onto the sample 9.

The means 15 comprise a capillary 16 containing the vapour source 10. The sample 9 is in powder form. As illustrated in the view from above in FIG. 24, the capillary 16 is in the form of a spiral. As illustrated in profile cross-section in FIG. 23, the capillary 16 is placed inserted in the top 13 of the pan, so that by closing the top 13 of the pan 77 onto the body of the pan, the end 21 of the capillary is lowered into the sample and diffuses solvent vapours inside the core of the sample, i.e. directly inside the sample in powder form. A capillary force holds said solvent in the capillary 16 and limits its diffusion in the system 8 around the sample.

The means 15 also comprise a stopper of material 17 situated at the end 21 of the capillary 16 through which the vapour 14 is diffused. The stopper 17 is a porous wall which separates the sample 9 and the part 18 of the capillary containing the vapour source 10, said wall 17 being arranged in order to limit the vapour diffusion 14 from the part 18 towards the sample of material 9. In other words, this wall 17 checks the passage of vapour of said solvent, from the capillary 16 towards the sample of material 9.

The means 15 are arranged so that the crystallization or recrystallization of the sample 9 commences only when the system 8 has reached the equilibrium temperature.

Finally, the device 5 also comprises the calculation means 19 previously described for calculating and determining a heat $Q_{crys}$ of crystallization or recrystallization and/or a mass of amorphous material m and/or an amorphous content T % of the sample 9, from a flow measurement $$P = \frac{dQ}{dt}$$

carried out by the measurement means.

FIG. 25 illustrates a second embodiment of a closed DSC pan for the second variant of a device according to the invention, which is described only for its differences with respect to the pan of FIG. 23. In this embodiment, the capillary is not inserted into the lid but emerges from the lid.

A description will now be given, with reference to FIG. 26, of a third variant of a device 53 according to the invention in an open system for implementing any one of the embodiments of the method according to the invention previously described. This third variant of a device 53 according to the invention in an open system is described only for its differences with respect to the device of FIG. 23. FIG. 26 does not show all the device 53, but only these differences with respect to the device of FIG. 23.

In this variant, the vapour source 10 is situated outside the system 8, in a container 31.

In this variant, the lid 13 is pierced so that the system 8 is not enclosed inside the pan 77; thus, the calorimeter 6 is arranged so that the sample of material 9 belongs to an open system 8, i.e. a system exchanging material. The system 8 gives up and receives a quantity of material with the outside the pan 77.

The means 15 comprise no stopper 17 but comprise a pump 32 situated outside the calorimeter, linking the container 31 to the system 8, and arranged for controlling and managing the vapour diffusion rate 14. The pump is arranged for injecting a carrier gas (such as air or nitrogen) saturated with the vapour 14 of the at least one crystallization solvent. The pump is arranged so that the diffusion rate of the vapour 14 is less than 100 nano moles per second, preferably comprised between 1 pico mole per second and 1 nano mole per second of the molecules of this vapour.

The device 53 also comprises means 33 of control of the pump arranged for adjusting the diffusion rate of the vapour 14 as a function of the response of the sample 9 (i.e. of the quantity of heat measured) during the hydration phase. More particularly, the means of control of the pump are arranged in order to commence the hydration phase with a high diffusion rate, then to reduce the diffusion rate over time so as not to cause crystallization during the hydration phase. Thus, the analysis time is reduced by speeding up the hydration phase while preventing crystallization during the hydration phase.

Moreover, the pan 77 and the sample are arranged so that the free volume 30 inside the pan 77, also called the dead volume, is less than 5% of the volume of the sample 9. Thus the exchanges between the molecules (for example of water) of the vapour phase 14 and the molecules expelled by the sample 9 during crystallization are significantly reduced.

Finally, the pump is arranged in order to inject the vapour 14 directly inside the sample 9 in powder form, which makes it possible to improve the crystallization of the sample.

FIG. 27 is a thermal activity curve of a sample of 6.82 mg, 6.69 mg or 6.70 mg of lyophilized lactose, obtained by the device according to the invention illustrated in FIG. 3. The crystallization solvent is only pure water. Crystallizations occur at 25° C., in a microcalorimeter ampoule 7, in a closed system, with a dead volume less than 5% of the volume of the sample. All the crystallizations started from zero and returned to zero to within a few tens of nanowatts (effect of the number of 10 μL nano-hygrostats).

Figure 28:
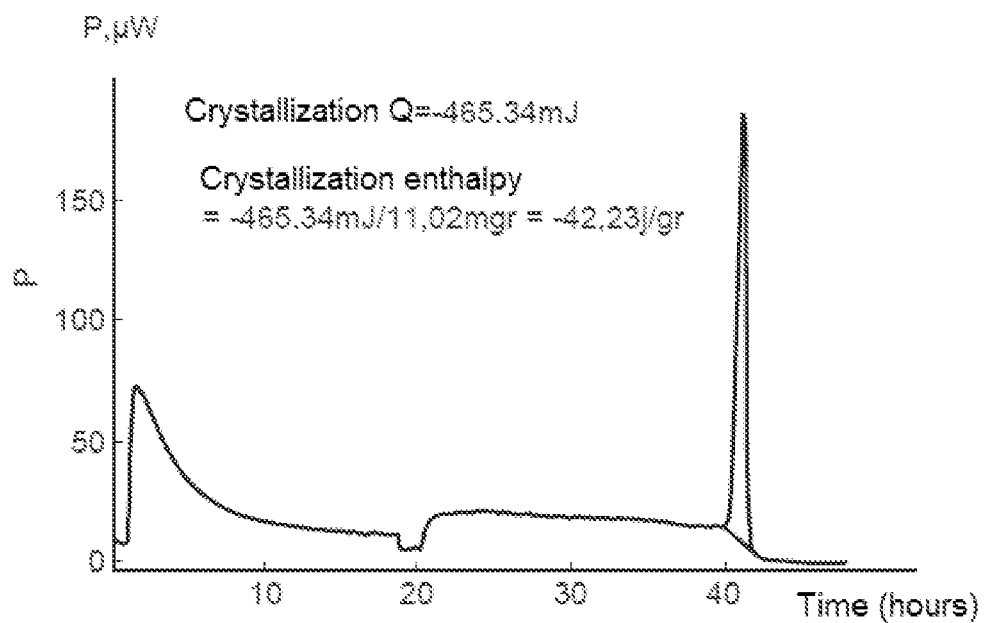
Figure 29:
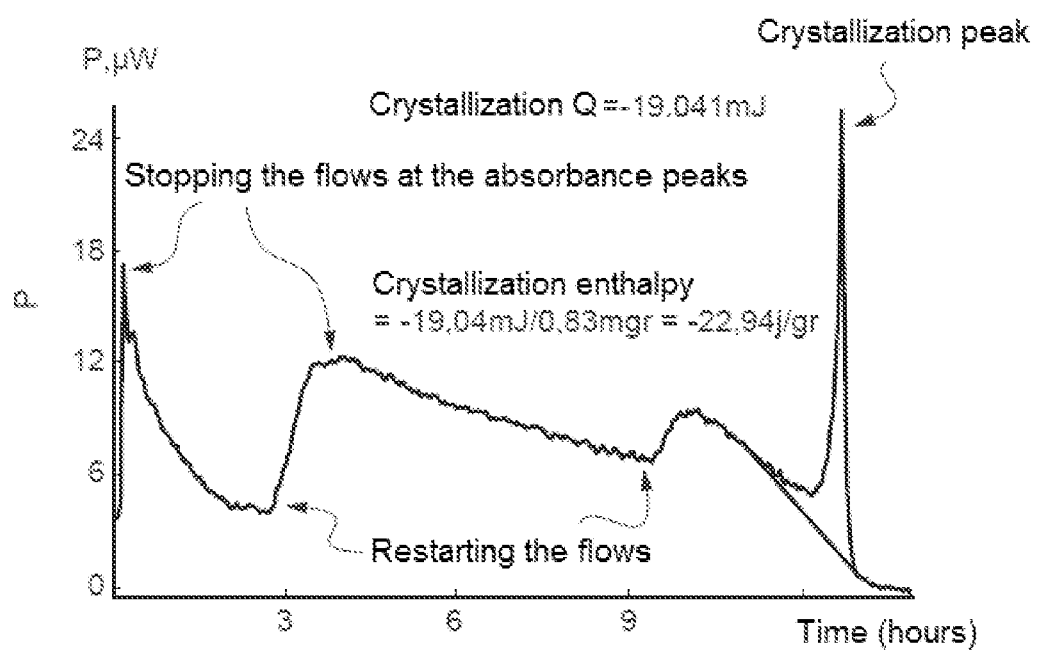

FIGS. 28 and 29 are thermal activity curves of a sample of amorphous lactose in a microcalorimeter ampoule 7 with a dead volume less than 5% of the volume of the sample, under 100% partial vapour pressure of crystallization solvents in an open system, obtained by the device according to the invention illustrated in FIG. 22.

In the case of FIG. 28, the crystallization solvent is pure water. FIG. 28 shows the crystallization, in water vapour, of 11.02 mg of amorphous lactose (obtained by lyophilization of a 5% lactose solution) in an open system (microcalorimetry under a flow of air at 100% relative humidity, 25° C.). The sample was maintained at 40% relative humidity (below its crystallization humidity) for 20 hours, then the relative humidity was increased to 100% with a flow of 20 nano moles of water/sec.

In the case of FIG. 29, the crystallization solvent is pure methanol. FIG. 29 shows the crystallization, in methanol vapour, of 0.83 mg of amorphous lactose (obtained by lyophilization of a 5% lactose solution) in an open system under a flow of air at 100% relative vapour pressure of methanol, and 25° C. The sample was maintained under a flow of 20 nano moles of methanol vapour/sec. When the sorption peak is reached, the flows are stopped and the powder is left to reach equilibrium by consuming the methanol vapours present in the ampoule, then when the sorption becomes low, the flows are resumed after stabilization of the sorption.

Figure 30:
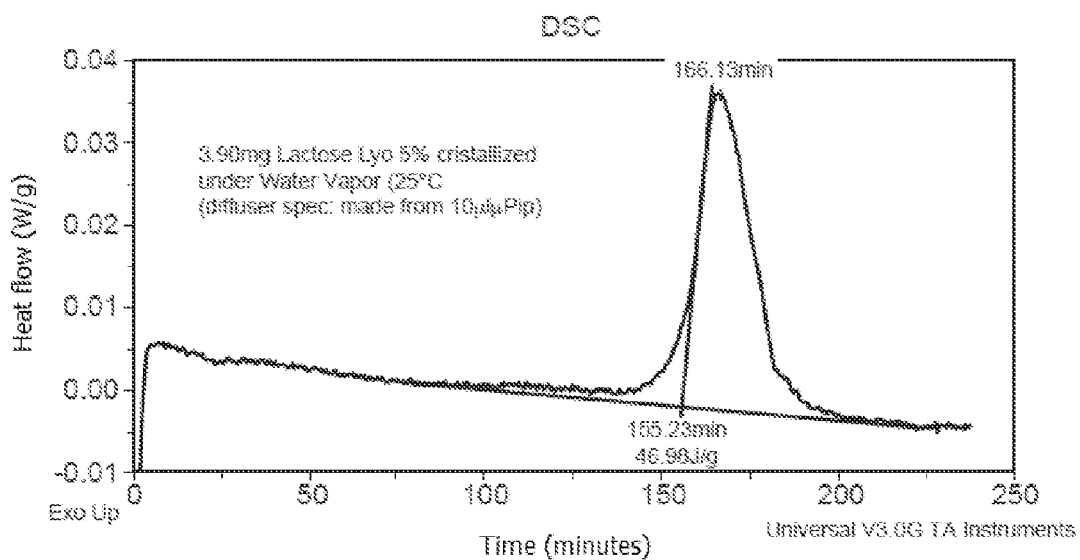
Figure 31:
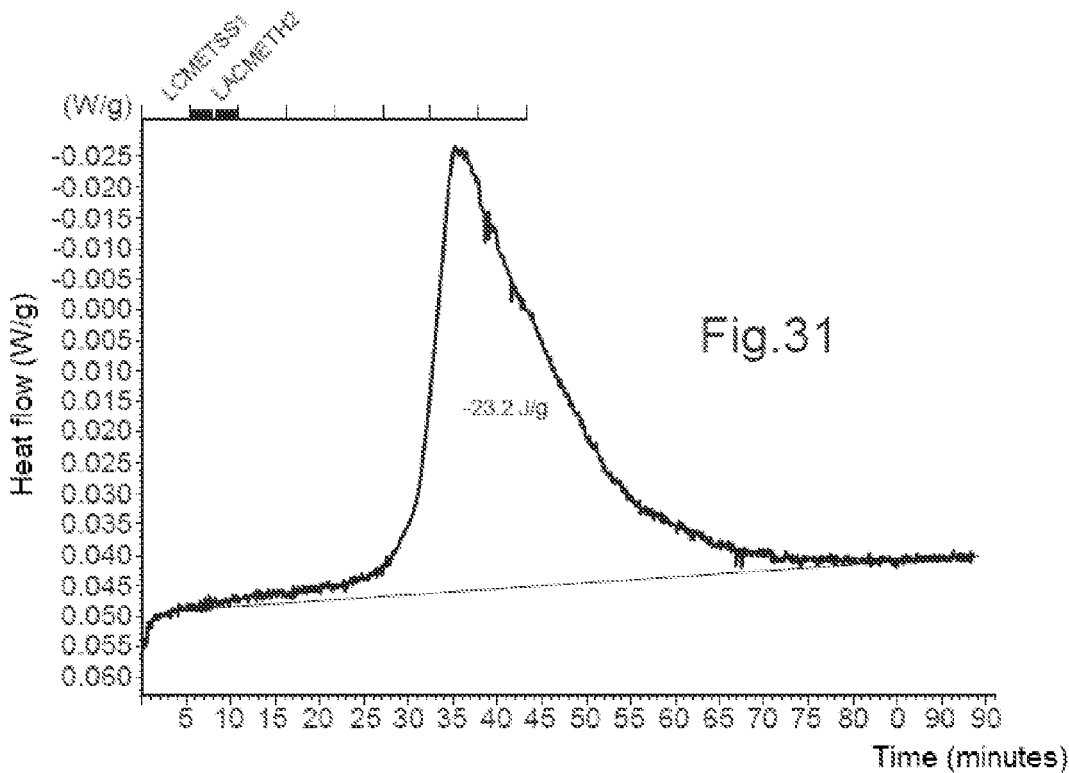
Figure 32:
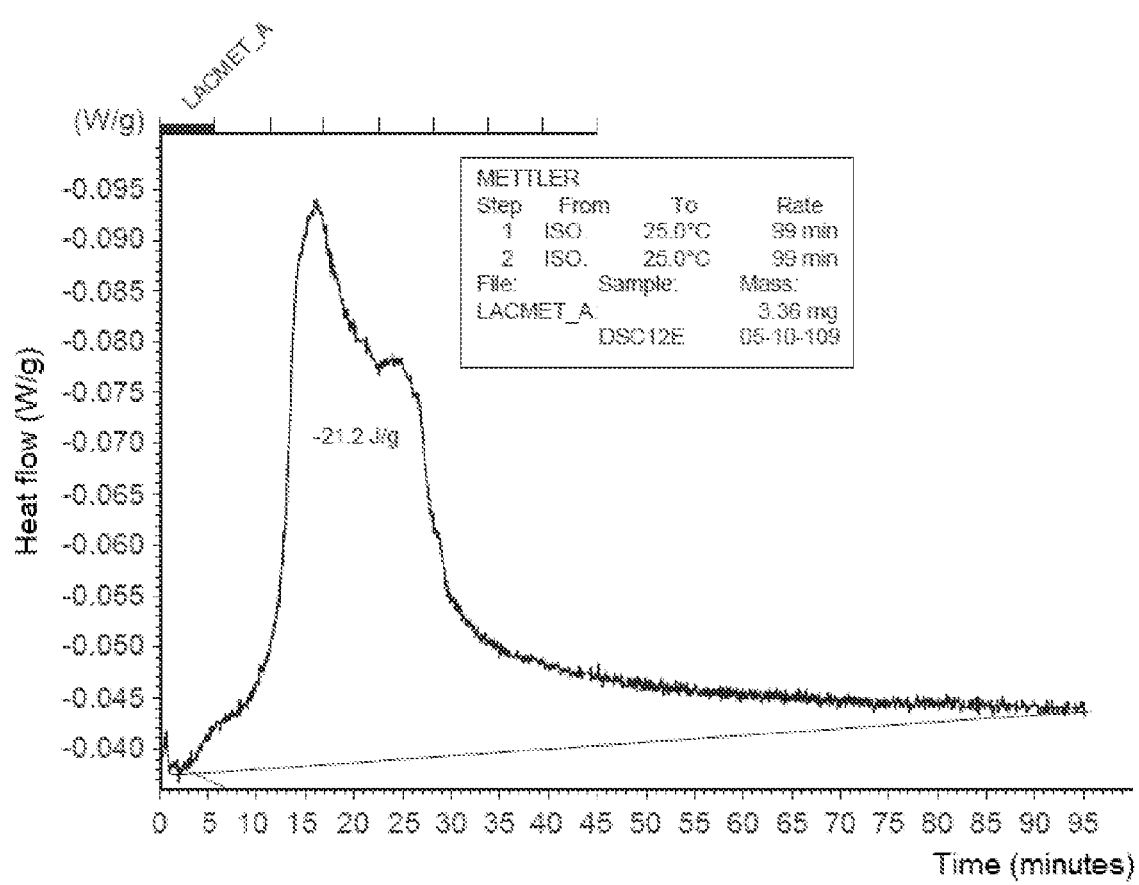

FIGS. 30, 31 and 32 are thermal activity curves of a sample of amorphous lactose in a pan of a DSC device with a dead volume less than 5% of the volume of the sample, in a closed system, obtained by the device according to the invention illustrated in FIG. 23.

FIG. 30 shows the crystallization using DSC of a sample of 3.9 mg of amorphous lactose crystallized under water vapour in a DSC from TA Instruments. The enthalpy of crystallization is equivalent to that found by microcalorimetry (Capillary containing 1 μL of crystallization solvent placed in the DSC pan used here in isothermal mode at 25° C.).

FIG. 31 shows a DSC thermogram (Mettler) of crystallization of 4.82 mg of amorphous lyophilized lactose under methanol vapour at 25° C. The enthalpy of crystallization of −23.2 J/g is very close to the value found by microcalorimetry for methanol.

FIG. 32 shows a DSC thermogram (Mettler) of crystallization of 3.36 mg of amorphous lyophilized lactose under methanol vapour at 25° C. The enthalpy of crystallization of −21.2 J/g is close to the value found by microcalorimetry for methanol.

It will be noted, in particular with reference to FIG. 29, that an advantage of the invention is that it is possible to measure an amorphous content very accurately even in a small quantity, typically of the order of a milligram for example, by detecting the heat of crystallization which can be clearly separated from other associated phenomena such as hydration, dissolution, etc.

The invention claimed is:

1. An isothermal system (8) to control the crystallization or recrystallization of a sample of solid material (9), which is initially at least partially amorphous and/or at least partially crystalline, contained in the system (8) with a vapour pressure, said isothermal system (8) comprising:
a vapour source for controlling the vapour pressure, said vapour source (10) comprising at least one solvent for crystallizing said solid material, the vapour diffusion (14) of which leads to crystallization or recrystallization of the sample (9), said vapour source (10) being such that the quantities of heat exchanged within the system during the crystallization or recrystallization of the sample (9) other than the heat of crystallization or recrystallization of the sample are less than approximately 10% of the heat of crystallization or recrystallization of the sample, and
means (15) of limiting the vapour diffusion (14), the means of limiting being arranged so that the vapour diffusion rate (14) is less than 100 nano moles per second.

2. The isothermal system according to claim 1, wherein the sample is comprised in a cell, the internal volume of which is adjusted to the volume of the sample such that the dead volume of the cell is less than 5% of the volume of the sample.

3. The isothermal system according to claim 1, wherein the vapour (14) is injected directly inside the sample (9) which is in powder form.

4. The isothermal system according to claim 1, wherein the vapour source (10) comprises a solute dissolved in said crystallization solvent, said solute being in a quantity less than the quantity necessary for the saturation of the solute in said solvent.

5. The isothermal system according to claim 1, wherein the vapour source (10) comprises a solute dissolved in said crystallization solvent, said solute being at saturation in said solvent, the solute dissolved in said solvent having a crystallization latency time greater than a crystallization or recrystallization latency time of the sample such that the solute crystallizes only after the end of crystallization or recrystallization of the sample.

6. The isothermal system according to claim 1, wherein the vapour source (10) comprises a solute dissolved in said crystallization solvent, said solute exhibiting no heat of solvation in said solvent.

7. The isothermal system according to claim 1, wherein said solvent in the vapour source (10) comprises no dissolved solute.

8. The isothermal system according to claim 1, wherein the vapour source (10) is a pure solvent or a mixture of solvents.

9. The isothermal system according to claim 1, wherein said solvent is selected from the group consisting of pure water, methanol, ethanol and mixtures thereof.

10. The isothermal system according to claim 1, wherein the sample of material (9) comprises an initially polymorphic or pseudo-polymorphic crystal, the recrystallization comprising passage from one crystalline phase to another crystalline phase of part or all of the sample.

11. The isothermal system according to claim 1, wherein the sample of material (9) initially comprises an amorphous and crystalline mixture.

12. The isothermal system according to claim 11, further comprising determination of the amorphous content of the sample.

13. The isothermal system according to claim 1, wherein the limitation of the diffusion rate is arranged so that the crystallization or recrystallization commences only when the system has reached an equilibrium temperature.

14. The isothermal system according to claim 1, wherein the vapour source (10) is contained in a capillary (16).

15. The isothermal system according to claim 1, wherein the vapour source (10) is absorbed in a support (25) which is not soluble in said crystallization solvent.

16. The isothermal system according to claim 1, wherein the vapour source (10) is contained in a reservoir (16, 22) separated from the sample (9) by a porous wall (17, 24) limiting the vapour diffusion (14) from the reservoir (16, 22) towards the sample of material (9).

17. A method for controlling crystallization or recrystallization comprising:
performing a vapour diffusion of at least one crystallization solvent in an isothermal system, said system comprising a sample of solid material and a vapour source diffusing the vapour, the solid material being initially at least partially amorphous and/or at least partially crystalline,
crystallizing or recrystallizing the sample under the effect of the diffused vapour,
at least during the crystallizing or recrystallizing, measuring heat received or given up by the system, the vapour source comprising said solvent for crystallizing said solid material, a method in which during the crystallization or recrystallization the quantities of heat exchanged within the system other than the heat of crystallization or recrystallization of the sample are less than approximately 10% of the heat of crystallization or recrystallization of the sample, and limiting a vapour diffusion rate in the system such that the vapour diffusion rate is less than 100 nano moles per second.

18. The method according to claim 17, wherein the sample is comprised in a cell, and the internal volume of which is adjusted to the volume of the sample such that the dead volume of the cell is less than 5% of the volume of the sample.

19. The method according to claim 17, wherein the vapour is injected directly inside the sample which is in powder form.

20. The method according to claim 17, wherein the vapour source comprises a solute dissolved in said crystallization solvent, said solute being in a quantity less than the quantity necessary for the saturation of the solute in said solvent.

21. The method according to claim 17, wherein the vapour source comprises a solute dissolved in said crystallization solvent, said solute being at saturation in said solvent, the solute dissolved in said solvent having a crystallization latency time greater than a crystallization or recrystallization latency time of the sample so that the solute crystallizes only after the end of crystallization or recrystallization of the sample.

22. The method according to claim 17, wherein the vapour source comprises a solute dissolved in said crystallization solvent, said solute exhibiting no heat of solvation in said solvent.

23. The method according to claim 17, wherein said solvent in the vapour source comprises no dissolved solute.

24. The method according to claim 17, wherein the vapour source is a pure solvent or a mixture of solvents.

25. The method according to claim 17, wherein said solvent is selected from the group consisting of pure water, methanol, ethanol and mixtures thereof.

26. The method according to claim 17, wherein the sample of material comprises an initially polymorphic or pseudo-polymorphic crystal, recrystallization comprising passage from one crystalline phase to another crystalline phase of part or all of the sample.

27. The method according to claim 17, wherein the sample of material initially comprises an amorphous and crystalline mixture.

28. The method according to claim 27, further comprising determining the amorphous content of the sample.

29. The method according to claim 17, wherein the heat measurement comprises measurement of the heat flow exchanged with the system or a measurement of the thermal activity of the system.

30. The method according to claim 17, wherein the vapour diffusion comprises a vapour diffusion of said crystallization solvent contained in a capillary.

31. The method according to claim 17, wherein the vapour diffusion comprises a vapour diffusion of said crystallization solvent absorbed in a support which is not soluble in this at least one solvent.

32. The method according to claim 17, wherein the vapour diffusion comprises a vapour diffusion of said crystallization solvent contained in a reservoir separated from sample by a porous wall limiting the vapour diffusion of the reservoir towards the sample of material.

33. The method according to claim 17, further comprising before the measurement a stabilization of the temperature of the system until the system reaches an equilibrium temperature, the system remaining at this equilibrium temperature during the measurement, the limitation of the diffusion rate being arranged so that the crystallization or recrystallization commences only when the system has reached the equilibrium temperature.

34. A device for controlling crystallization or recrystallization for implementing a method according to claim 17, comprising:
means (6, 7) for receiving a sample of solid material (9) which is initially at least partially amorphous and/or at least partially crystalline and for receiving a vapour source (10) comprising at least one solvent for crystallizing said solid material, the reception means (6, 7) being arranged so that the sample of material and the vapour source form an isothermal system (8), the reception means (6, 7) being moreover arranged so that vapour (14) diffused by the source (10) initiates crystallization or recrystallization of the sample (9),
means (11) for measuring heat received or given up by the system, and
means (15) for limiting a vapour diffusion rate (14) in the system (8), the means of limitation being arranged so that the vapour diffusion rate (14) is less than 100 nano moles per second.

35. The device according to claim 34, wherein the means of limitation are arranged so that the vapour diffusion rate (14) is less than 100 nano moles per second.

36. The device according to claim 34, further comprising a cell, this cell being arranged for receiving the sample and so that its internal volume can be adjusted to the volume of the sample so that the dead volume of the cell is less than 5% of the volume of the sample.

37. The device according to claim 34, further comprising means for injecting the vapour (14) directly inside the sample (9) which is in powder form.

38. The device according to claim 34, wherein the means (15) of limiting the diffusion rate include a capillary (16) provided to contain the vapour source (10).

39. The device according to claim 34, wherein the means (15) of limiting the diffusion rate include a support (25) which is not soluble in said solvent and provided for absorbing the vapour source (10).

40. The device according to claim 34, wherein the means (15) of limiting the diffusion rate include a porous wall (17, 24) separating the sample (9) and a reservoir (16, 22) provided for containing the vapour source (10), said wall (17, 24) being arranged in order to limit the vapour diffusion from the reservoir (16, 22) towards the sample of material (9).

41. The device according to claim 34, wherein the reception means include means (11) for stabilizing a temperature of the system until the system reaches an equilibrium temperature, the means (15) of limiting the diffusion rate being arranged so that the crystallization or recrystallization of the sample commences only when the system has reached the equilibrium temperature.

42. The device according to claim 34, further comprising means (19) for determining an amorphous content of the sample, from a measurement carried out by the measurement means.

43. The isothermal system according to claim 1, wherein the quantities of heat exchanged within the system during the crystallization or recrystallization of the sample (9) other than the heat of crystallization or recrystallization of the sample are less than approximately 5%.

44. The isothermal system according to claim 1, wherein the quantities of heat exchanged within the system during the crystallization or recrystallization of the sample (9) other than the heat of crystallization or recrystallization of the sample are less than approximately 1%.

45. The isothermal system according to claim 2, wherein said cell is a microcalorimetric ampoule or a DSC pan.

46. The isothermal system according to claim 8, wherein said solvent is selected from the group consisting of pure water and an organic solvent.

47. The method according to claim 17, wherein the quantities of heat exchanged within the system other than the heat of crystallization or recrystallization of the sample are less than approximately 5% of the heat of crystallization or recrystallization of the sample.

48. The method according to claim 17, wherein the quantities of heat exchanged within the system other than the heat of crystallization or recrystallization of the sample are less than approximately 1% of the heat of crystallization or recrystallization of the sample.

49. The method according to claim 18, wherein said cell is a microcalorimetric ampoule or a DSC pan.

50. The method according to claim 36, wherein said cell is a microcalorimetric ampoule or a DSC pan.

* * * * *